(12) United States Patent
Goldstein et al.

(10) Patent No.: US 8,462,956 B2
(45) Date of Patent: Jun. 11, 2013

(54) EARHEALTH MONITORING SYSTEM AND METHOD IV

(75) Inventors: Steven W. Goldstein, Delray Beach, FL (US); John Usher, Montreal (CA); Brian Fligor, Mansfield, MA (US); John P. Keady, Boca Raton, FL (US)

(73) Assignee: Personics Holdings Inc., Boca Raton, FL (US)

( * ) Notice: Subject to any disclaimer, the term of this patent is extended or adjusted under 35 U.S.C. 154(b) by 1391 days.

(21) Appl. No.: 11/931,252

(22) Filed: Oct. 31, 2007

(65) Prior Publication Data

US 2008/0144842 A1    Jun. 19, 2008

Related U.S. Application Data

(63) Continuation-in-part of application No. 11/757,152, filed on Jun. 1, 2007, now Pat. No. 8,311,228.

(60) Provisional application No. 60/803,708, filed on Jun. 1, 2006.

(51) Int. Cl.
*H04R 29/00* (2006.01)
*H04R 25/02* (2006.01)
*G06F 17/00* (2006.01)
*G01C 3/08* (2006.01)

(52) U.S. Cl.
USPC ............... 381/56; 73/645; 181/130; 700/94

(58) Field of Classification Search
USPC .......... 700/94; 381/56–60, 71.6, 328; 600/25, 600/559; 73/1.82, 585, 645, 646; 181/130
See application file for complete search history.

(56) References Cited

U.S. PATENT DOCUMENTS

| | | | |
|---|---|---|---|
| 3,802,535 A | 4/1974 | Peake | |
| 3,987,245 A | 10/1976 | Fasen et al. | |
| 4,554,639 A | 11/1985 | Baker et al. | |
| 4,947,432 A | 8/1990 | Topholm | |
| 5,430,826 A | 7/1995 | Webster et al. | |
| 5,692,059 A * | 11/1997 | Kruger ......................... | 381/151 |
| 5,757,930 A | 5/1998 | Seidemann et al. | |

(Continued)

FOREIGN PATENT DOCUMENTS

| | | |
|---|---|---|
| EP | 165468 A1 | 12/1985 |
| EP | 1615468 | 1/2006 |
| GB | 2098733 | 11/1982 |
| WO | 2006002055 | 1/2006 |

OTHER PUBLICATIONS

OSHA, "Occupational Noise Exposure", Jul. 1, 2005, Section 1910. 95, pp. 211-223.

(Continued)

*Primary Examiner* — Jesse Elbin
(74) *Attorney, Agent, or Firm* — RatnerPrestia

(57) ABSTRACT

A system for monitoring sound pressure levels at the ear includes an ambient sound microphone (ASM) for receiving ambient sounds and an ear canal microphone (ECM) for producing audio signals as a function of ambient sound received at the ambient sound microphone and a sound signal received from an associated personal audio device. A logic circuit is operatively associated with the ASM and ECM calculates a total SPL_Dose experienced by the ear at a time t. The total SPL_Dose is calculated by determining SPL_Dose for periods Δt as measured at the ECM. The logic circuit may select an action parameter in response to the Total SPL_Dose.

3 Claims, 17 Drawing Sheets

U.S. PATENT DOCUMENTS

| | | |
|---|---|---|
| 6,379,314 B1 | 4/2002 | Horn |
| 6,456,199 B1 | 9/2002 | Michael |
| 6,473,512 B1 | 10/2002 | Juneau et al. |
| 6,648,820 B1 | 11/2003 | Sarel |
| 6,754,359 B1 * | 6/2004 | Svean et al. .................. 381/328 |
| 6,826,515 B2 | 11/2004 | Bernardi et al. |
| 6,840,908 B2 | 1/2005 | Edwards et al. |
| 7,756,281 B2 | 7/2010 | Goldstein et al. |
| 2003/0002688 A1 | 1/2003 | Kanevsky et al. |
| 2003/0165246 A1 * | 9/2003 | Kvaloy et al. ................. 381/312 |
| 2005/0020873 A1 | 1/2005 | Berrang et al. |
| 2005/0100169 A1 | 5/2005 | Shelley et al. |
| 2005/0117765 A1 | 6/2005 | Meyer et al. |
| 2005/0250439 A1 | 11/2005 | Leslie |
| 2005/0254665 A1 | 11/2005 | Vaudrey et al. |
| 2005/0254667 A1 | 11/2005 | Michael |
| 2006/0137934 A1 | 6/2006 | Kurth |
| 2007/0129828 A1 | 6/2007 | Lee et al. |
| 2007/0147624 A1 | 6/2007 | Fischer |
| 2007/0270988 A1 | 11/2007 | Goldstein et al. |
| 2008/0194984 A1 | 8/2008 | Keefe |

OTHER PUBLICATIONS

Part 380 Occupational Noise Exposure, Michigan Occupational Safety and Health Administration, 2004.

Final Office Action for U.S. Appl. No. 11/763,281, filed Jun. 14, 2007, mailed Jun. 20, 2012.

Office Action for U.S. Appl. No. 11/763,281, filed Jun. 14, 2007, mailed Oct. 14, 2011.

Office Action for U.S. Appl. No. 11/763,281, flied Jun. 14, 2007, mailed Apr. 4, 2011.

Extended European Search Report for European Application No. 07798583.6, dated Jan. 4, 2013.

* cited by examiner

EARHEALTH MONITORING SYSTEM AND METHOD IV

CROSS-REFERENCE TO RELATED APPLICATIONS

This application is a Continuation-in-Part of U.S. patent application Ser. No. 11/757,152 filed on 1 Jun. 2007, now U.S. Pat. No. 8,311,228 the disclosure of which is incorporated herein by reference in its entirety, which in turn claims priority from U.S. Provisional Application No. 60/803,708 filed on 1 Jun. 2006.

FIELD OF THE INVENTION

The present invention relates to a device that monitors acoustic energy directed to an ear, and more particularly, though not exclusively, to an earpiece that monitors acoustic sound pressure level dose received by a user's ear.

BACKGROUND OF THE INVENTION

With the advent of an industrial society, people are exposed to noise pollution at greater and greater levels; both from background, such as street traffic, airplanes, construction sites and intentional exposure to high sound levels such as cell phones, MP3 players, and rock concerts. Studies show that ear damage, leading to permanent hearing impairment is not only increasing in the general population, but increasing at a significantly faster rate in younger populations.

The potential for hearing damage is a function of both the level and the duration of exposure to the sound stimulus. Safe listening durations at various loudness levels are known, and can be calculated by averaging audio output levels over time to yield a time-weighted average. Standard damage-risk guidelines published by OSHA, NIOSH or other agencies are known. This calculation can be even further improved by or accounting for aspects of the playback scenario, specifically the characteristics of the sound source and their proximity to the listener's ear.

Studies have also indicated that hearing damage is a cumulative phenomenon. Although hearing damage due to industrial or background noise exposure is more thoroughly understood, the risk of exposing one's self to excessive noise, especially with the use of headphones has also been recently studied. Protecting the ear from ambient noise is primarily done with the use of static earplugs that attempt to shield the inner ear from excessively high decibel noise. Background noise canceling earphones such as those produced by Bose and others, attempt to protect the ear from excessive ambient noise by producing a counter noise wave to cancel out the ambient noise at the ear. These prior art devices have been less than satisfactory because they do not completely prevent high decibel noise from reaching the ear, and do not account for the duration of exposure to harmful sounds at the ear.

It is also known from the prior art to provide active noise reduction at the ear to protect the ear from exposure to loud noises as disclosed in U.S. patent Application No. US2005/0254665. The art actively attenuating noise reaching the inner ear utilizing a control; a connection with an earpiece and attenuating the noise to the ear. However, there is no monitoring of the noise over time to account for the cumulative effect. Furthermore, there is no accounting for any restorative effects within the ear for sound level exposures, which are sufficiently low to allow recovery, rather than destruction.

Dosimeters, such as that described in U.S. published Application No. US2005/0254667 are known. The device periodically measures prior sound level in the ambient environment. However, the device does not take into account the cumulative effect of the noise over multiple incidences of exposure (e.g., one day to the next) or the effect of any restorative period. Furthermore, no remedial action is automatically taken as a result of the readings.

It is also known from the prior art that headphones for consumer electronics have been provided with a predetermined maximum output level in an attempt to prevent ear damage. This approach is ineffective as it does not take into account listening duration and the calculation of risk for auditory injury. Other headphones are maximum-limited to produce levels that can still result in significant overexposure given enough time, or limit the user to levels, which may not be sufficient to achieve an adequate short term listening level. In the latter case, consumer acceptance for the protective gear could be severely limited and a product would fail to survive in a competitive market and therefore be of no use.

Another alternative known in the art is to reduce the headphone output levels by increasing earphone impedance via an accessory placed between the media player and the earphones. The limitation of this approach is that it gives no consideration to the duration of exposure, and again either the user's chosen listening level cannot be achieved because the maximum level is too limited, or the level is sufficient to allow the user access to high enough sound levels, but risk overexposure due to potential duration of use.

It is known from U.S. Publication No. 2007/0129828 to provide automated control of audio volume parameters in order to protect hearing. A method of operating a media player includes the step of playing back audio media and refining a maximum volume parameter for the playing of the media by the media player. The refining is based at least in part on the playback of audio media during a time period existing prior to the execution of refining the maximum volume allowed. The refinement is intended to minimize harm to the user's hearing.

Applicants cannot confirm that such an approach has been commercialized. However, even if commercialized, it suffers from the shortcomings that the refinement is based on a theoretical noise volume delivered to the ear as a function of the output signal of the device and parameters of the earpiece connected to the device and is based upon a credit system based on volume. There is no measurement of the actual noise delivered to the ear. Furthermore, the calculation does not take into account the ambient noise of the device user or the noise reduction rate of the earpiece relative to the ambient noise. In other words, the actual volume level to which the ear is exposed is not taken into account. Accordingly, a severe miscalculation of the actual ear expose, and resulting ear harm, may exist as a result of use of this related art method. Additionally the credit system is not described in detail sufficient for one of ordinary skill to construct the device. For example U.S. Publication No. 2007/0129828 refers to Cal-OSHA profiles, and states in the same paragraph that Cal-OSHA appear to be rudimentary and does not deal with exposure "in a sophisticated way with varying exposure over time" and does not " . . . account for recovery." However, U.S. Publication No. 2007/0129828 states in one example " . . . the maximum allowed volume is determined based upon determined credits with reference to a profile such as profiles provided by . . . (Cal-OSHA) . . . " However, U.S. Publication No. 2007/0129828, stated that Cal-OSHA doesn't take into effect recovery, and additionally fails to refer to any detailed recovery calculation.

Accordingly, a system that overcomes the shortcomings in the related art would be useful.

BRIEF SUMMARY OF THE INVENTION

A system for monitoring sound pressure levels at the ear includes an ambient sound microphone (ASM) for receiving ambient sounds and an ear canal microphone (ECM) for producing audio signals as a function of ambient sound received at the ambient sound microphone and sound signal received from an associated personal audio device. A logic circuit is operatively associated with the ASM and ECM calculates a total SPL_Dose experienced by the ear at a time t.

In one exemplary embodiment the total SPL_Dose is calculated by determining SPL_Dose for periods Δt as measured at the ECM. The logic circuit may then select an action parameter in response to the Total SPL_Dose.

DETAILED DESCRIPTION OF THE INVENTION

Figure 1:
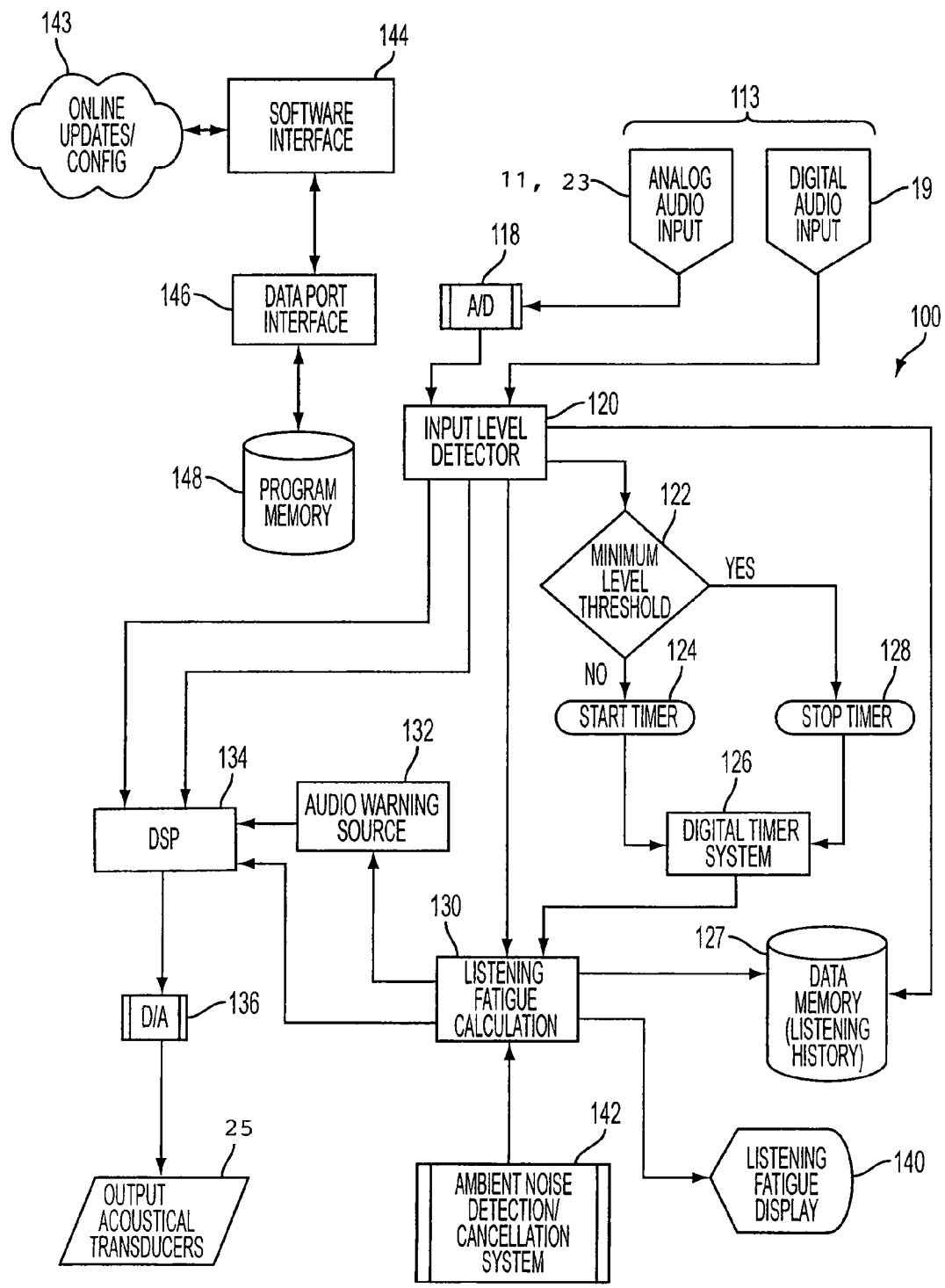
FIG. 1 is a block diagram of the system for measuring and determining exposure to sound over time at the ear constructed in accordance with a first exemplary embodiment of the invention.

The following description of at least one exemplary embodiment is merely illustrative in nature and is in no way intended to limit the invention, its application, or uses.

Processes, techniques, apparatus, and materials as known by one of ordinary skill in the relevant art may not be discussed in detail but are intended to be part of the enabling description where appropriate, for example the fabrication and use of transducers. Additionally in at least one exemplary embodiment the sampling rate of the transducers can be varied to pick up pulses of sound, for example less than 50 milliseconds.

In all of the examples illustrated and discussed herein, any specific values, for example the sound pressure level change, should be interpreted to be illustrative only and non-limiting. Thus, other examples of the exemplary embodiments could have different values.

Note that similar reference numerals and letters refer to similar items in the following figures, and thus once an item is defined in one figure, it may not be discussed for following figures.

Note that herein when referring to correcting or preventing an error or damage (e.g., hearing damage), a reduction of the damage or error and/or a correction of the damage or error are intended.

Figure 2:
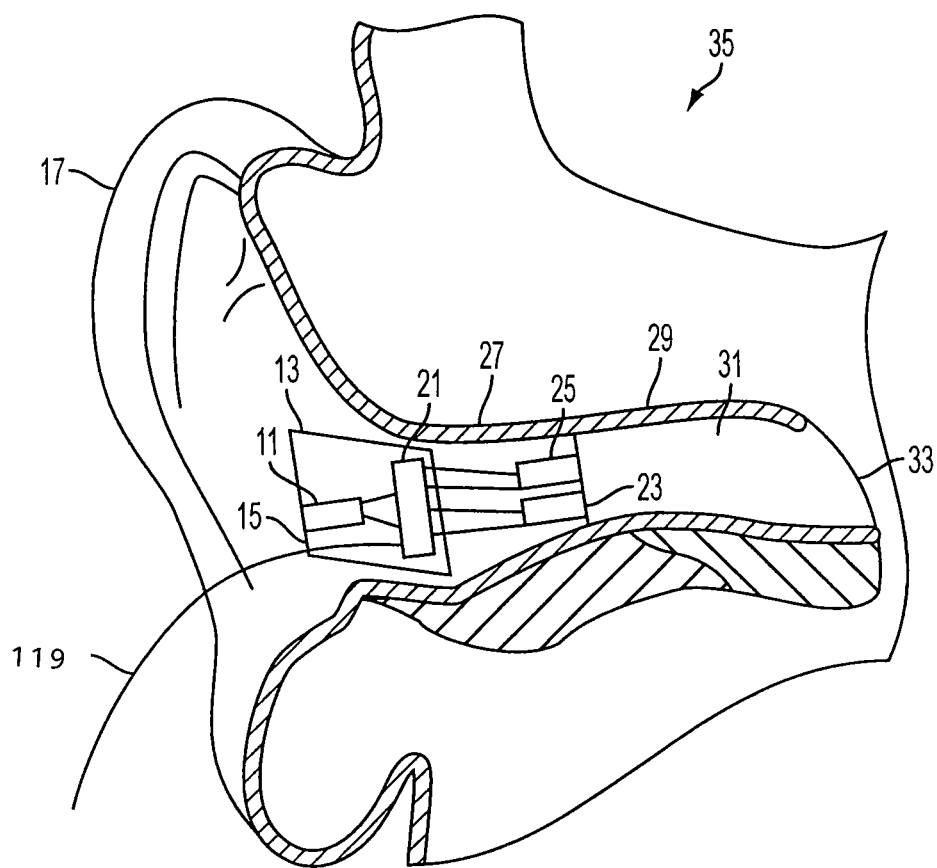
FIG. 2 is a block diagram of the system in accordance with at least one exemplary embodiment of the invention in situ in the ear.

At least one exemplary embodiment of the invention is directed to measuring and determining the exposure of the ear to sound over time. Reference is made to FIG. 1 in which a system, generally indicated as 100, is constructed in accordance with at least one exemplary embodiment of the invention. System 100 includes an audio input device 113 for receiving sound at the ear. As will be discussed below, audio input device 113 can include an analog audio input 11, 23 and a digital audio input 19. In at least one exemplary embodiment, audio input device 113 receives audio input from at least one of three sources, namely; ambient noise around the ear, direct input noise such as a MP3 player or other device which can produce a digital audio input at digital audio input 19, and noise as detected within the ear canal 31 (FIG. 2). The audio input device 113 outputs an audio signal corresponding to the received sound. Analog output signals from analog audio inputs 11, 23 are converted to a digital signal by an analog-to-digital (ND) converter 118 so that digital sound signals are input into an input level detector 120.

Input level detector 120 determines the sound pressure level of the sound received at audio input device 113. Input level detector 120 outputs a sound pressure level (SPL) signal, which is input to a minimum-level threshold detector 122. Minimum level threshold detector 122 determines whether or not the sound pressure level as detected by input level detector 120 exceeds a minimum level threshold. As will be discussed below, the minimum level threshold can be the permissible sound level PSL (e.g., effective quiet level) of the individual, or some predetermined level substantially corresponding to a level, which is ear damage neutral over time, or a level of interest, such as 80 dB, because of its effect on the ear. Therefore, if the minimum level threshold is detected as being exceeded, a signal indicating a sound pressure level in excess of the minimum level threshold is output to a start timer 124, which triggers a digital timer system 126 to begin a clock. Conversely, if the input sound pressure level is detected as being below the minimum threshold, a signal indicating the sound pressure level is below the minimum level threshold is output to a start timer 124, which triggers a digital timer system 126 to begin a clock of a restorative period. If the sound pressure level is at the minimum threshold (within a margin of error), no clock needs to be started because this is neutral to the desired effect. In a preferred embodiment, the clock signal is changed with every significant (more than 1 dB by way of example) change in sound pressure level to get an accurate profile of sound exposure over time.

Once the sound pressure level as detected at input level detector 120 decreases to or is below the minimum threshold level, a stop timer signal is output from stop timer 128 to digital timer system 126 to stop the clock corresponding to exposure to the excessively intense level. Digital timer system 126 outputs a clock value corresponding to the time period at which the minimum level threshold was not met, or in the preferred embodiment, for each period corresponding to a discrete level change.

A data memory or learning history database 127 receives the clock value from digital timer system 126 as well as the actual input level detected at input level detector 120 and determines a listening history or sound pressure level exposure history. The sound pressure level exposure history is a record of the user's exposure to sound pressure levels over time. Because the effect of exposure is cumulative, it is important that the exposure history be maintained. The listening history, as will be discussed below, can include real ear level data, listening duration data, time between listening sessions, absolute time, sound pressure level dose (SPL_Dose) data, including any restorative sound level, number of acoustic transients and crest factor and other data.

The sound pressure level exposure history or listening history includes both the listening habits history and the environmental or ambient noise exposure history. The environmental noise exposure history is the exposure of a user to environmental noise over time as a result of the auditory stimuli inherent to the environment where the user is present. This can be highway traffic, construction site, even the restorative effect of the quiet sound pressure levels, e.g., those typically encountered in a library whereas, the listening habits history is associated for the purposes for this disclosure with user-directed auditory stimuli such as music, words, other noises, which a user intentionally encounters for a purpose such as communication, learning, and enjoyment. Therefore, database 127, as will be discussed below, stores the cumulative SPL exposure.

It should be noted that in at least one exemplary embodiment, minimum level threshold detector 122 also starts the timer 124 when the sound pressure level is below the predetermined level. In this way, the restorative effect of sound levels below PSL (e.g., effective quiet noise) is accumulated for determining overall exposure damage potential.

In effect, the only time that digital timer system 126 is not running is when the detected sound pressure level signal is at the minimum level threshold. A listening fatigue calculator 130 receives the input level signal from input level detector 120 and data from the data memory listening history 127, and determines whether or not listening fatigue or hearing damage is likely to occur as a result of further exposure. Hearing damage is the injury to the hearing mechanism including conductive and sensorineural decrement in hearing threshold levels. It can be either temporary or permanent so long as it is a result of the noise exposure that is above PSL (e.g., Effective Quiet). In other words, listening fatigue calculator 130 will output a signal when a threshold sound exposure, determined as a function of exposure time and sound pressure level, as will be discussed in greater detail below, is achieved. At that point, a listening fatigue signal is output.

It should be noted that in an alternative embodiment, system 100 can make use of an ambient noise detection/cancellation system 142 as known in the art. These systems produce signals, which cancel sound pressure levels at certain frequencies and/or certain levels to reduce the effect of undesired noise, whether environmental noise or user directed noise. It will have some effect in elongating the permissible exposure time by negating the sound pressure level detected by input level detector 120.

In at least one exemplary embodiment, the signal from the listening fatigue calculator is utilized to prevent damage and encourages some action by the user when exposure levels are near damaging levels. Therefore, in one non-limiting example, a listening fatigue display 140 is provided for receiving the signal from the listening fatigue calculator and displaying to the user a prompt to discontinue exposure to the sound level from the damaging sound source or audio source.

In another non-limiting example, the signal from the listening fatigue calculator is output to an audio warning source 132, which outputs an output audio warning to the user notifying the user that exposure to the sound source has reached critical levels.

In at least one exemplary, but non-limiting, embodiment, as will be discussed below, system 100 includes an output acoustical transducer 25 to provide an audio signal to the ear. Output acoustical transducer 25 operates under the control of a digital signal processor (DSP) 134. Digital signal processor 134 receives a digital audio signal from input level detector 120, which acts as a pass through for the digitized signals from audio input device 113. Digital signal processor 134 passes the sound signals through to a digital to analog (D/A) converter 136 to drive acoustical transducers 25 to recreate the sound received at audio input device 113 inside the ear canal 31 in at least one exemplary embodiment of the invention as shown in FIG. 2. With such an exemplary embodiment, audio warning source 132 provides an output to digital sound processor 134 causing output acoustical transducer 25 to output a warning sound inside the ear of the user.

Additionally, in at least one further exemplary embodiment, listening fatigue calculator 130 outputs a listening fatigue signal to digital processor 134 which causes digital signal processor 134 to attenuate the sound signal prior to output to acoustical transducer 25 to reduce the signal output level by any of the linear gain reduction, dynamic range reduction, a combination of both, or a complete shutdown of transducer 25. Attenuation would be at least to the level, if not below, the PSL (e.g., effective quiet level) to allow for ear recovery prior to damage.

It should be noted, that because personal hearing threshold and discomfort levels can change from person to person, and because both of the time intervals are a function of many variables, in a non-limiting example, to provide a dynamic ever-changing response, system 100 operates under software control. The configuration of the digital sound processor 134, listening fatigue calculator 130, the minimum level threshold detector 122, and the input level detector 120 are operated under software control.

In an exemplary embodiment of the invention, the control programs are stored in a program memory 148 for operating the firmware/hardware identified above. Furthermore, the program stored within memory 148 can be personalized as a result of testing of the user's ear, or by other modeling methods, in which system 100 includes a software interface 144 for receiving online or remote source updates and configurations.

The software interface 144 communicates with a data port interface 146 within system 100, which allows the input of software updates to program memory 148. The updates can be transmitted across a distributed communications network, such as the Internet, where the updates take the form of online updates and configurations 143.

It should be noted that there is multiple functionality distributed across system 100. In at least one exemplary embodiment, at least audio input device 113 and acoustical transducer 25 are formed as an earpiece, which extends into the outer ear canal so that the processing of signals pertains to sound received at the ear. However, it is well within the scope of at least one exemplary embodiment of the invention to provide substantially all of the functionality in an earpiece so that system 100 is a "smart device."

Also note that when referring to measurements in decibels (dB) one is referring to a logarithmic ratio. For example dB is defined as:

$$SPL = \beta(d\beta) = 10\log\frac{I}{I_0} = 10\log\frac{\Delta P^2}{\Delta P_0^2} \quad (1)$$

Where I is the intensity measured, $I_0$ is a reference intensity, $I_0 = 10^{-12}$ W/m$^2$, and $P_0$ is a reference pressure, $\Delta P_0 = 20$ micropascals, and where $\Delta P$ is the root mean squared pressure amplitude in a measured pressure wave (e.g., using a transducer). Thus, the sound pressure level (SPL) can be measured in dB.

Alternatively, one can use the above equation and solve for measured pressures instead. For example:

$$\Delta P(t) = 10^{(SPL(t)/20.0)} \Delta P_0 \quad (2)$$

In the discussion of formulas herein we refer to SPL as a non-limiting example and one of ordinary skill in the arts could re-derive the equations in terms of measured pressures, $\Delta P$, both are intended to lie within the scope of at least one exemplary embodiment. Reference is now made to FIG. 2 in which system 100 in which the transducer configuration, that portion of system 100, which converts sound pressure level variations into electrical voltages or vice versa is shown. In this embodiment, acoustic transducers include microphones as an input and loudspeakers as an acoustical output.

FIG. 2 depicts the electro acoustical assembly 13 (also referred to herein as an in-the-ear acoustic assembly 13 or earpiece 13), as it would typically be placed in the ear canal 31 of ear 17 of user 35. The assembly is designed to be inserted into the user's ear canal 31, and to form an acoustic seal with the walls 29 of the ear canal 31 at a location 27, between the entrance 15 to the ear canal and the tympanic membrane or eardrum 33. Such a seal is typically achieved by means of a soft and compliant housing of assembly 13. A seal is critical to the performance of the system in that it creates a closed cavity in ear canal 31 of approximately 0.5 cc in a non-limiting example between the in-ear assembly 13 and the ear's tympanic membrane 33.

As a result of this seal, the output transducer (speaker) 25 is able to generate a full range bass response when reproducing sounds for the system user. This seal also serves to significantly reduce the sound pressure level at the user's eardrum 33 resulting from the free/diffuse sound field at the entrance 15 to the ear canal 31. This seal is also the basis for the sound isolating performance of the electroacoustic assembly 13. Located adjacent to speaker 25, is an ear canal microphone (ECM) 23, which is also acoustically coupled to closed cavity 31. One of its functions is that of measuring the sound pressure level in cavity 31 as a part of testing the hearing sensitivity of the user as well as confirming the integrity of the acoustic seal and the working condition of itself and speaker 25. Audio input 11 (also referred to herein as ambient sound microphone (ASM) 11) is housed in assembly 13 and monitors sound pressure at the entrance 15 to the occluded ear canal. The transducers can receive or transmit audio signals to an ASIC 21 that undertakes at least a portion of the audio signal processing described above and provides a transceiver for audio via the wired or wireless communication path 119.

In the above description the operation of system 100 is driven by sound pressure level, i.e. sound levels are monitored for time periods or epochs during which the sound pressure level does not equal the minimum level threshold or is constant. However, as will be discussed in connection with the next exemplary embodiments of the invention, system 100 can also operate utilizing fixed or variable sampling epochs determined as a function of one or more of time and changes in sound pressure level, sound pressure level dosage, weighting functions to the sound pressure level, and restorative properties of the ear.

Figure 3:
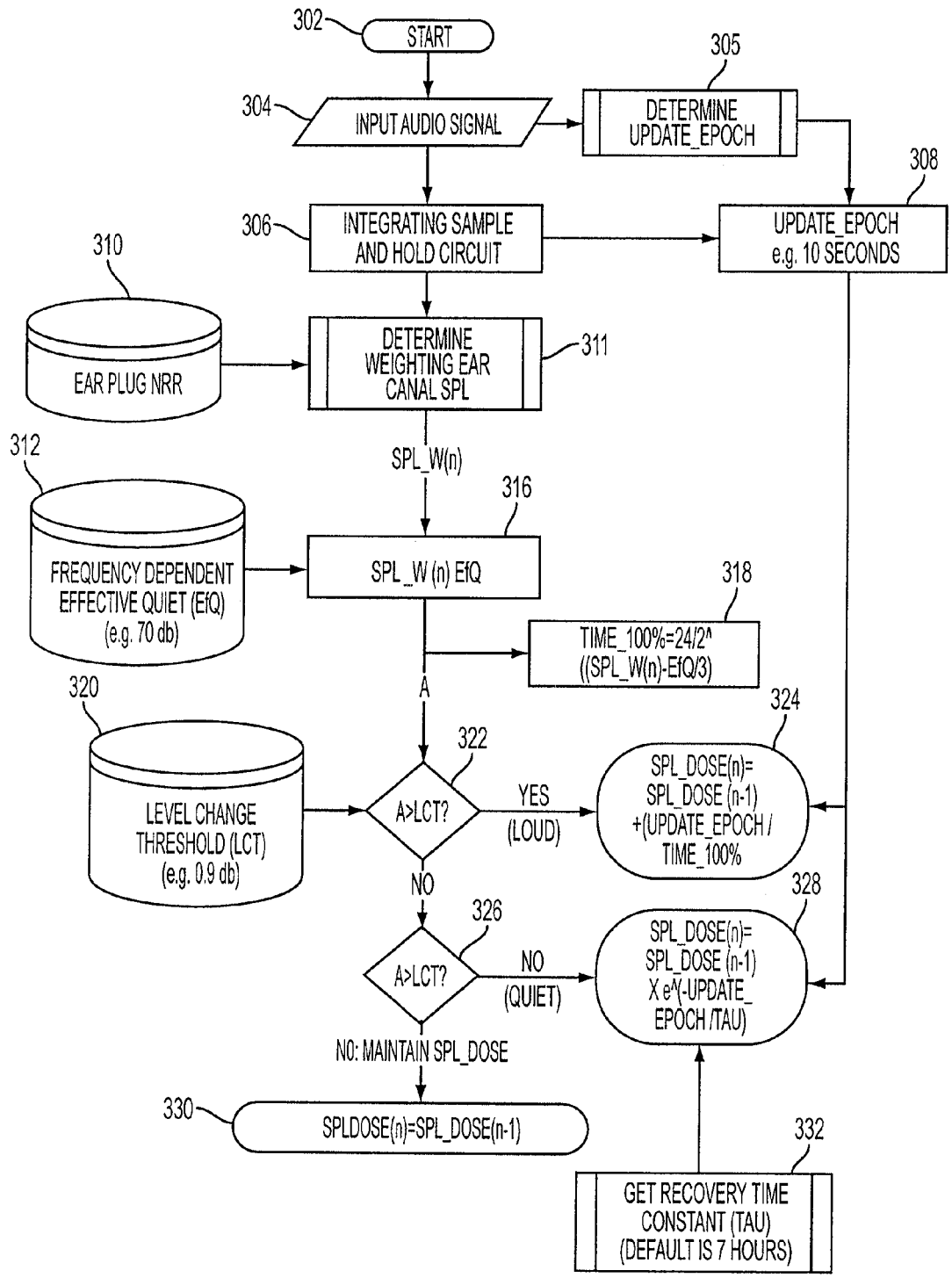
FIG. 3 is a flow chart for calculating listening fatigue in accordance with at least one embodiment of the invention by measuring a quantity (e.g., the sound pressure level) over time as received at the ear.

Reference is now made to FIG. 3 in which a flow chart for monitoring the sound pressure level dose at various sample times n is provided. The process is started in a step 302. An input audio signal is generated in a step 304 at either the ear canal microphone (ECM) 23 or the ambient sound microphone (ASM) 11. Changes in SPL_Dose resulting from duration of exposure time is a function of the sound pressure level, therefore, the epoch or time period used to measure ear exposure or, more importantly, the time-period for sampling sound pressure level is determined in a step 305. The update epoch is used in the SPL_Dose function determination as well as to effect the integration period for the sound pressure level calculation that, as will be discussed below, is used to calculate the weighted ear canal sound pressure level.

Figure 6:
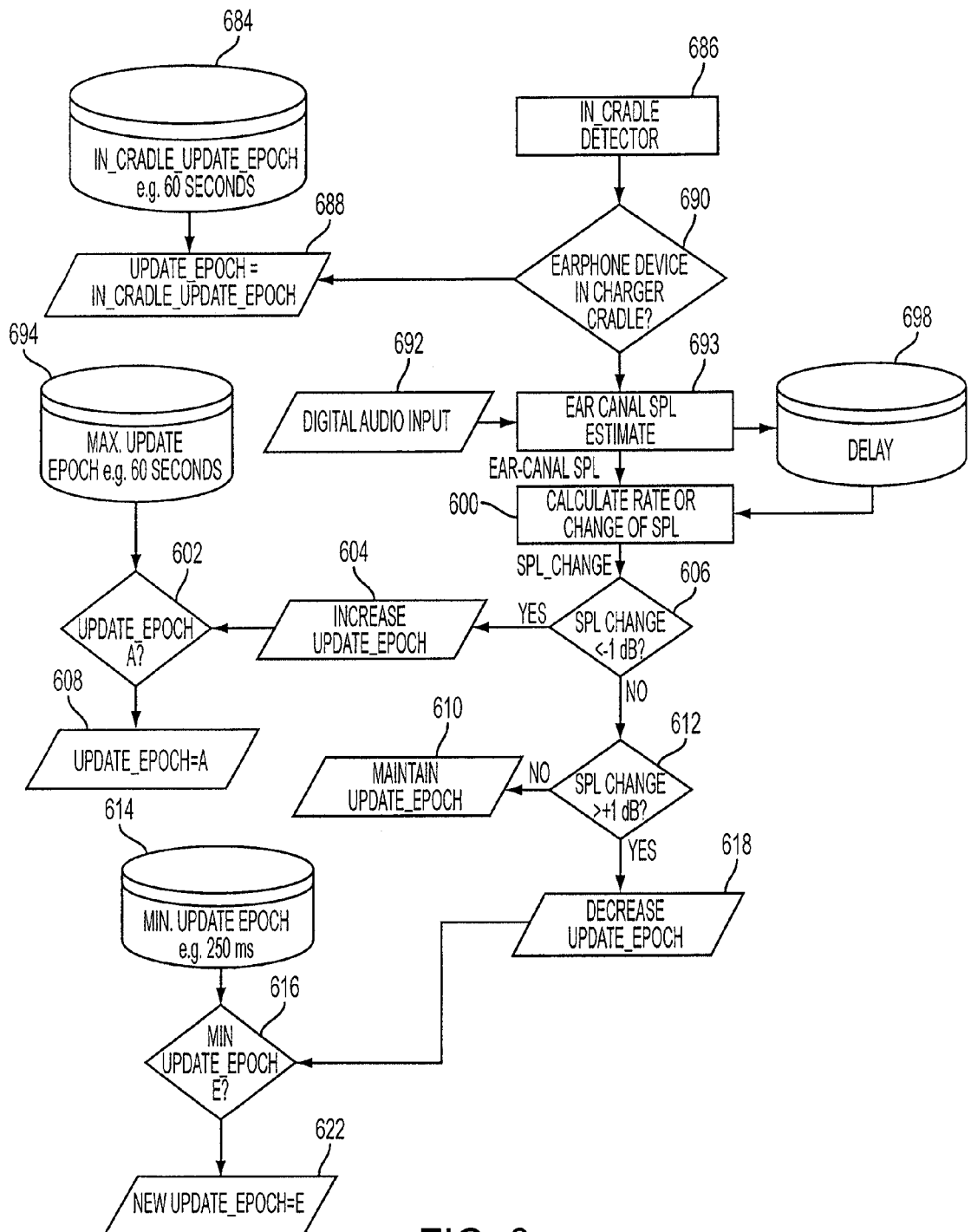
FIG. 6 is a flow chart for determining an update epoch in accordance with at least one exemplary embodiment of the invention.
Figure 7:
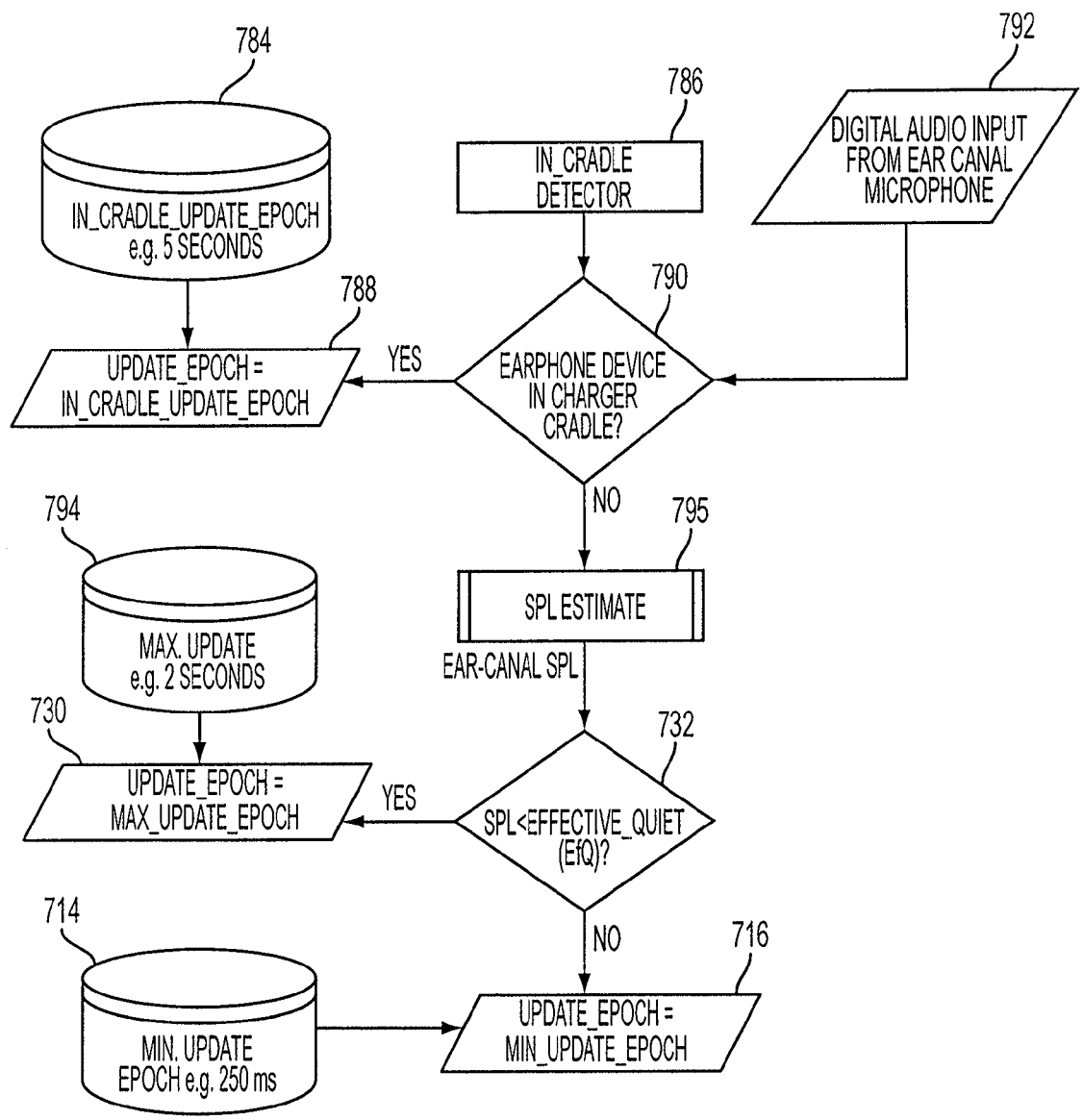
FIG. 7 is a flow chart for determining an update epoch in accordance with yet another exemplary embodiment of the invention.

Reference is now made to FIGS. 6 and 7. In FIG. 6, a method is defined to change the update epoch as a function of the weighted ear canal sound pressure level, which will be discussed in greater detail below. System 100 is capable of determining when earpiece 13 is in a charger or communication cradle (i.e., not in use in the ear of the user). In a step 684, a predetermined standard is provided for the update epoch, 60 seconds in this example. In step 688, the update epoch is set as the in-cradle update epoch. The in-cradle state is detected in step 686. If it is determined in a step 690 earpiece 13 (also referred to herein as earphone device 13) is in a charger or cradle mode, then the update epoch is set as the in-cradle epoch; in the step 688.

However, if in step 690 it is determined that the earphone device 13 is in use, in other words "not in the cradle", then, by default, an audio signal is input to earpiece 13 in step 692. In step 693, an ear canal sound pressure level is estimated as a function of the audio input at step 692. The current (n) ear canal sound pressure level estimate is stored as a delay level in a step 698. An audio input is determined at a later time when step 692 is repeated so that a second in-time ear canal sound pressure level estimate is determined.

In a step 600, the delayed (n−1) or previous sound pressure level is compared with the current (n) ear canal sound pressure level estimate to calculate a rate of change of the sound pressure level. The change level is calculated in units of dB per second. This process of step 692 through 600 is periodically repeated.

In a step 606, it is determined whether or not the sound pressure level change is less than a predetermined amount (substantially 1 dB by way of non-limiting example) between iterations, i.e., since the last time the ear canal sound pressure level is calculated. If the change is less than the predetermined amount, then in step 604 the update epoch is increased. It is then determined in a step 602 whether or not the epoch update is greater than a predefined amount D set in step 694 as a maximum update epoch such as 60 seconds in a non-limiting example. If in fact, the update epoch has a value greater than the maximum update epoch D then the update epoch is set at the higher value D in step 608.

If it is determined in step 606 that the sound pressure level change is, in a non-limiting example, greater than −1 dB, but less than +1 dB as determined in step 612, then the update epoch value is maintained in a step 610. However, if it is determined that the sound pressure level change is, in a non-limiting example, greater than +1 dB, then the update epoch value is decreased in a step 618 to obtain more frequent sampling. A minimum predetermined update epoch value such as 250 microseconds is set in a step 614. If the decreased update epoch determined in step 618 is less than, in other words an even smaller minimum time-period than the predetermined minimum update epoch E, then the new update epoch is set as the new minimum update epoch value in steps 616 and 622. In this way, the sample period is continuously being adjusted as a function of the change in sound pressure level at the ear. As a result, if the noise is of a transient variety as opposed to a constant value, the sampling interval will be changed to detect such transients (e.g., spikes) and can protect the ear.

Reference is now made to FIG. 7 in which a method for changing the update epoch is illustrated as a function of the way that the ear canal sound pressure level estimate is provided. Again, in accordance with at least one exemplary embodiment of the invention, the update epoch is decreased when the ear canal sound pressure level is high or increasing.

The difference between the embodiment of FIG. 7 and the embodiment of FIG. 6 is that the update epoch is not continuously adjusted, but is more static. If the ear canal sound pressure level is less than PSL (e.g., effective quiet, a decibel level which when the ear is exposed to over time does not damage or facilitate restoration the ear), then the update epoch is fixed at a predefined maximum epoch value and this is the value used by system 100 as will be discussed in connection with FIG. 3 below. A system for monitoring sound pressure levels at the ear includes an ambient sound microphone for receiving ambient sounds and an ear canal microphone for producing audio signals as a function of ambient sound received at the ambient sound microphone and sound signal received from an associated personal audio device. A logic circuit is operatively associated with the ASM and calculates a Total SPL_Dose experienced by the ear at a time t.

In one exemplary embodiment the Total SPL_Dose is calculated by determining estimated SPL_Dose for periods Δt. The logic circuit may then select an action parameter in response to the Total SPL_Dose. If it is determined to be greater than a permissible (or permitted) sound level (PSL) (e.g., effective quiet), then the update epoch is fixed at a shorter minimum value and this is returned as the update epoch to be utilized.

In FIG. 7, specifically, as with FIG. 6, an in-cradle update epoch of 5 seconds by way of non-limiting example, is stored in system 100 in a step 784. In a step 788, the initial update epoch is set as the in-cradle update epoch. A maximum update epoch time, such as 2 seconds by way of non-limiting example, is stored in a step 794. In a step 714, an initial minimum update epoch (250 microseconds in this non-limiting example) is stored.

In a step 786 and step 790 it is determined whether or not system 100 is in a non-use state, i.e., being charged or in a cradle. If so, then the update epoch is set at the in-cradle update epoch. If not, then a digital audio signal is input from ear canal microphone 23 in step 792. A sound pressure level is estimated in step 795. It is then determined whether or not the ear canal sound pressure level is less than PSL (e.g., effective quiet) in a step 732. If the sound pressure level is less than the PSL (e.g., effective quiet) as determined in step 732, then the update epoch is set at the maximum update epoch in a step 730. If the sound pressure level is more intense than the effective quiet, then in step 716, the update epoch is set to the minimum update epoch.

Returning to FIG. 3, in a non-limiting exemplary embodiment, the update epoch is set at 10 seconds in a step 302 utilizing either a constant predetermined sample time, or either of the methodologies discussed above in connection with FIGS. 6 and 7. In a step 306, the input audio signal is sampled, held, and integrated over the duration of the epoch as determined in step 308. As a result, the update epoch affects the integration period utilized to calculate the sound pressure level dose as a function of the sound pressure level and/or as the weighted ear canal sound pressure level.

In a step 310, an earplug noise reduction rating (NRR) is stored. The noise reduction rating corresponds to the attenuation effect of earpiece 13, or system 100, on sound as it is received at audio input 11 and output at the output transducer 25 or as it passes from the outer ear to the inner ear, if any exemplary embodiment has no ambient sound microphone 11. In a step 311, a weighted ear canal sound pressure level is determined, partially as a function of the earplug noise reduction rating value.

Figure 4:
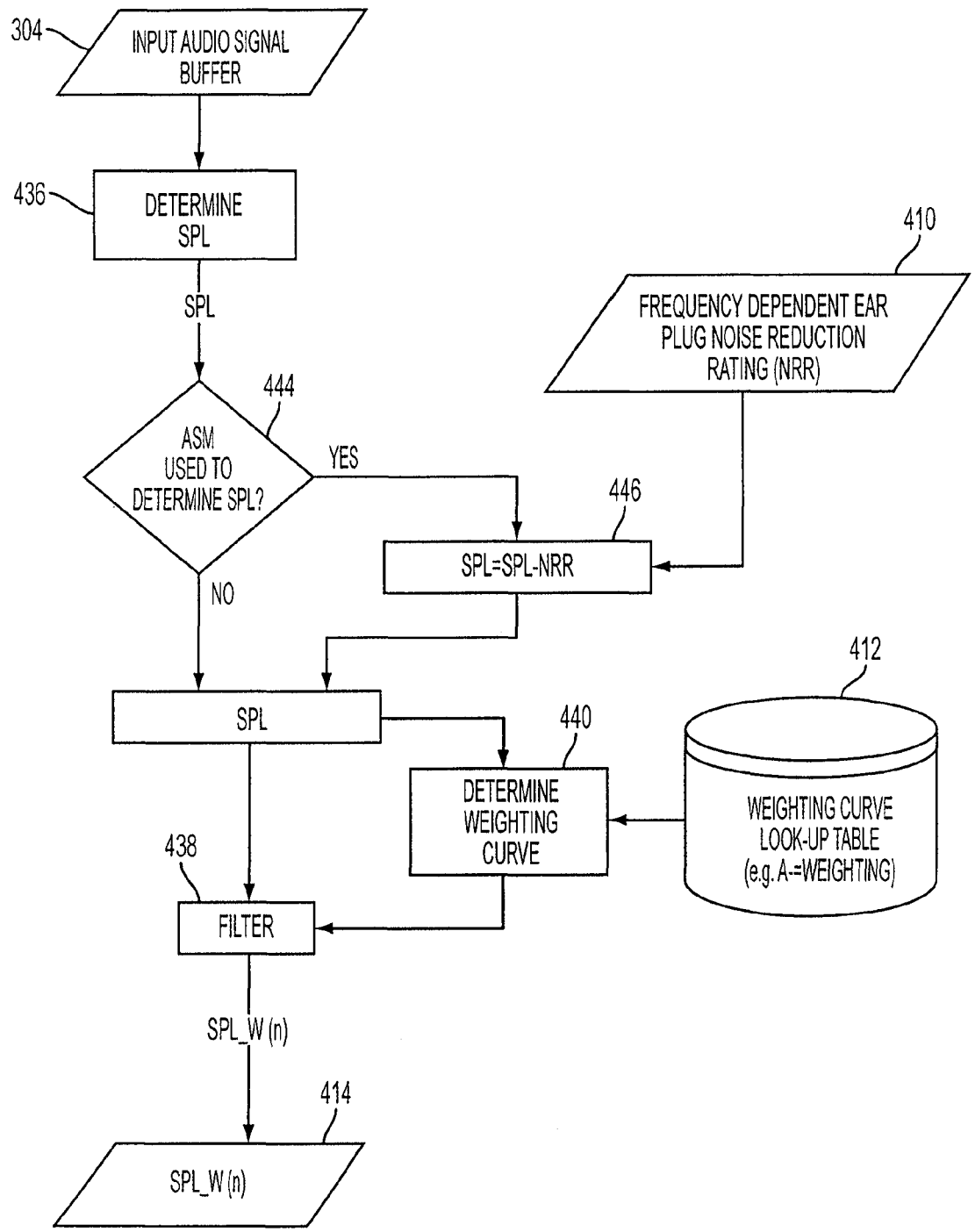
FIG. 4 is a flow chart for determining a weighted ear canal sound pressure level in accordance with another exemplary embodiment of the invention.

Reference is now made to FIG. 4 where a method for determining the weighted ear canal sound pressure level in accordance with at least one exemplary embodiment of the invention is illustrated. Like numerals are utilized to indicate like structure for ease of discussion and understanding. Weighting is done to compensate for the manner in which sound is perceived by the ear as a function of frequency and pressure level. As sounds increase in intensity, the auditory perception of loudness of lower frequencies increases in a nonlinear fashion. By weighting, if the level of the sound in the sound field is low, the methodology and system utilized by at least one exemplary embodiment of the invention reduces the low frequency and high frequency sounds to better replicate the sound as perceived by the ear.

Specifically, a weighting curve lookup table, such as A-weighting, acts as a virtual band-pass filter for frequencies at sound pressure levels. In a step 304, the audio signal is input. In step 410, frequency-dependent earplug noise reduction ratings are stored. These values are frequency-dependent and in most cases, set as manufacturer-specific characteristics.

As discussed above, in a step 306, the input audio signal is shaped, buffered and integrated over the duration of each epoch. The sound pressure level of the shaped signal is then determined in a step 436. It is determined whether or not ambient sound microphone (ASM) 11 was utilized to determine the sound pressure level in a step 444. If microphone 11 was utilized, then the frequency-dependent earplug noise reduction rating of earpiece 13 must be accounted for to determine the sound level within the ear. Therefore, the noise reduction rating, as stored in step 310, is utilized with the sound pressure level to determine a true sound pressure level (at step 446) as follows:

$$SPL_{ACT} = SPL - NRR: \qquad (3)$$

where sound pressure $SPL_{ACT}$ is the actual sound pressure level received at the ear medial to the ECR, SPL is the sound pressure level determined in step 436 and NRR is the noise reduction rating value stored in step 410.

If the ambient sound microphone (ASM) 11 is not used to determine the sound pressure level then the sound pressure level determined in step 436 is the actual sound pressure level. So that:

$$SPL_{ACT} = SPL \quad (4)$$

It is well within the scope of at least one exemplary embodiment of the invention to utilize the actual sound pressure level as determined so far to determine the affect of the sound pressure level received at the ear on the health of the ear. However, in at least one exemplary embodiment, the sound pressure level is weighted to better emulate the sound as received at the ear. Therefore, in a step 412, a weighting curve lookup table is stored within system 100. In a step 440, the weighting curve is determined as a function of the actual sound pressure level as calculated or determined above in steps 436, 446 utilizing a weighting curve lookup table such as the A-weighting curve. The A-weighting curve is then applied as a filter in step 438 to the actual sound pressure level. A weighted sound pressure level value representative of a sampled time period (SPL_W(n)) is obtained to be utilized in a step 414.

The weighting curve can be determined in step 440 by applying a frequency domain multiplication of the sound pressure level vector and the weighting curve stored in step 412. In this exemplary embodiment, the weighting curve would be appropriate for direct multiplication with the SPL in the frequency domain (i.e., SPL(f)). In another exemplary embodiment the weighted SPL can be expressed as a weighting of the measured pressure vector as:

$$SPL\_W(n)(t) = 20 \log\left(\frac{\Delta P^{W_A}(t)}{\Delta P_0}\right) \quad (5)$$

where $\Delta P(t)$ is the measured temporal change in root mean squared pressure, which can be converted into spectral space (e.g., FFT) as $\Delta P(f)$ which is the measured spectral change in pressure, which can in turn be multiplied by a weighting function (e.g., A-weighting), $W_A(f)$) and expressed as $\Delta P^{W_A}(f) = \Delta P(f) \cdot W_A(f)$, and then reconverted (e.g., inverse FFT) into temporal space to obtain $\Delta P^{W_A}(t)$. To obtain a single value various integration or summation over the n-th time interval (e.g., which can change in time) can be performed. For example:
]

$$SPL\_W(n) = \frac{1}{\Delta t_n} \int_{t_{n-1}}^{t_n} 10\log\left(\frac{(\Delta P^{W_A}(t))^2}{\Delta P_0^2}\right) dt \quad (6)$$

The time during which a user may be exposed to the sound level SPL_W(n), i.e. the time to 100% allowable dosage at SPL level SPL_W(n), is referred to below as Time__100%(n).

The weighting curves can be stored as a lookup table on computer memory, or can be calculated algorithmically. Alternatively, the input audio signal can be filtered with a time or frequency domain filter utilizing the weighting curve stored in step 412 and the sound pressure level as calculated. For low-level sound pressure levels, those less than 50 dB, by way of non-limiting example, a weighting curve, which attenuates low and high frequencies can be applied (similar to an A-weighting curve). For higher sound pressure levels, such as more than 80 dB, by way of non-limiting example, the weighting curve can be substantially flat or a C-weighting curve. The resulting weighted ear canal sound pressure level during any respective sampling epoch is returned as the system output SPL_W(n) in step 414. Note that herein various conventional weighting schemes are discussed (e.g., A-weighting, C-weighting) however in at least one exemplary embodiment non-conventional weighting schemes can be used. For example, generally the threshold level of hearing sensitivity (threshold of detection) is referenced in dB, where 20 micropascals is typically used as the minimum threshold level of pressure variation that an average normal-hearing person can detect. This reference value tends to be used at all frequencies, although the threshold level varies with frequency. Thus, one weighting scheme is to adjust the reference 0 dB level on a frequency basis, by using a conventional dB of threshold hearing chart, which provides the dB (f) at threshold level. A weighting function can be used where the value is about 1 at the reference value (e.g., equivalent to 20 micropascals) at a reference frequency (e.g., 1000 Hz). The other values (e.g., as a function of frequency) of the weighting function can vary depending upon the reference threshold pressure variation for the particular frequency, for example if at 30 Hz the threshold level in dB is 65 dB, then the weighting value can be 1/65 at 30 Hz, de-emphasizing the loudness and/or intensity at 65 dB when SPL_Dose (f) is calculated.

Returning to FIG. 3, a safe listening time is calculated by comparing the weighted sound pressure level with the PSL (e.g., effective quiet level) in step 316. Therefore, a value A corresponding to how far from safe listening the sound pressure level is, is determined by the equation:

$$A = SPL\_W(n) - PSL \quad (7)$$

where PSL is the permissible sound level, for example PSL=EfQ, where EfQ is equal to the sound level of effective quiet (as stored at step 312). However, PSL can be any level chosen for the particular circumstance, for example lower than EfQ.

By utilizing this simple comparative function, fewer machinations and processes are needed. System 100 takes advantage of the fact that because the PSL (e.g., effective quiet level) can be neutral to the ear, sound pressure levels significantly above the PSL (e.g., effective quiet level) are generally damaging and noise levels below the PSL (e.g., effective quiet) generally allow for restoration/recovery.

In step 318, the remaining safe listening time at the beginning of any current sampling epoch can be calculated by Time__100% minus the time duration of exposure up to the current sampling epoch. Note that a negative number can occur, indicating that no safe listening time remains. The estimated time (e.g., in hours) until the individual's sound exposure is such that permanent threshold shift may occur, ignoring any previous sound exposure and assuming that the SPL of the sound field exposed to individual remains at a constant level L can be calculated as follows:

$$\text{Time}\_100\%(n) = T_c/(2^{((SPL\_W(n)-PSL)/ER)}); \quad (8)$$

Where PSL is the permissible sound level, and Tc is the critical time period. For example, if Tc (Critical Time) is 8 hours and PSL is 90 dBA and ER (the Exchange Rate) is 5 dB, then that accepts that ~22-29% of people are at risk for hearing loss. If Tc is 8 hours and PSL is 85 dBA and ER is 3 dB, then that accepts that ~7-15% of people are at risk, likewise for if Tc is 24 hours and PSL is 80 dBA and ER is 3 dB, same 7-15% at risk. Thus Time__100% (n) reflects a reduction of the risk to a chosen level. Note that $T_c$ is the critical time period of exposure that one is looking at (e.g., 8 hours, 24 hours), and ER is the exchange rate, for example can be expressed as:

$$\text{Time\_100\%}(n) = 8(\text{hours})/(2^{((\text{SPL\_}W(n)-85\ \text{dBA})/3\ \text{dB}))} \quad (9)$$

These values assume a recovery period of 16 hours at a SPL during that time of less than 75 dBA (where dBA refers to Decibels of an A-weighted value). Of course the realism of such an assumption is questionable given music, TV, and other listening habits of individuals. Thus, we are concerned with exposure over a 24-hour period. Thus, Time_100% (n) can be expressed for a 24 hour period (e.g., $T_c$=24 (hours)), where, for example using an equal energy assumption (i.e., ER of 3 dBA), as:

$$\text{Time\_100\%}(n) = 24/(2^{((\text{SPL\_}W(n)-\text{PSL})/3)}). \quad (10)$$

Another further example is the situation where PSL=EfQ, where the Effective Quiet, EfQ is defined as the highest sound level that does not cause temporary or permanent hearing threshold shift, nor does it impede recovery from temporary hearing threshold shift. For broadband noise, it can be 76-78 dBA, although these numbers can be different or refined over time based upon research and/or measurement history.

As a non-limiting example, the lower bound of SPL_W(n) dictating the Time_100% equation would be SPL_W(n)=PSL, and the upper bound of the SPL_W(n) dictating Time_100% equation would be about SPL_W(n)=115 dB.

Note that in at least one exemplary embodiment, the acoustic signals measured by an ECM or an ECR in ECM mode, can be used to detect a user's voice, for example using the technology discussed in Webster et al., U.S. Pat. No. 5,430, 826, incorporated by reference in its entirety. If voice is detected then by the magnitude of the SPL (e.g., 80 dB) one can tell whether the user is speaking as compared to a non-user's voice (e.g., 50 dB) that has been attenuated by the earpiece. When a user's voice is detected then SPL_W(n) can be reduced by an amount (DSPL, e.g., 20 dB) that is due to Stapedius (Middle-ear Muscle) Reflex (e.g., when the user's voice triggers a muscle response in the muscles supporting the ossicles transmitting sound from the eardrum to cochlea), effectively damping some of the sound. Thus SPL_W(n)$_{new}$=SPL_W(n)−DSPL, where SPL_W(n)$_{new}$ is used in the Time_100% (n) equation as opposed to SPL_W(n).

In this embodiment, rather than make use of the Sound Level (L), the period is a function of the intensity (both high and low) of the weighted sound pressure level. It should be noted that PSL (e.g., effective quiet) is used in the above example, but any level of interest, such as 80 dB, or no sound level, i.e., SPL_W(n)−0, can be used. The weighted sound pressure level and PSL can be expressed as a frequency-dependent numerical array or a value scalar.

It is next determined whether or not the difference between the current weighted sound pressure level and the PSL (e.g., effective quiet) is above a tolerable threshold for risk of hearing damage or not, i.e., whether the weighted SPL in the eardrum is considered to increase risk for hearing damage or not. A sound pressure level dose is calculated depending upon whether the sound level is sufficiently intense or not. The sound pressure level dose (SPL_Dose) is the measurement, which indicates an individual's cumulative exposure to sound pressure levels over time. It accounts for exposure to direct inputs such as MP3 players, phones, radios and other acoustic electronic devices, as well as exposure to environmental or background noise, also referred to as ambient noise. The SPL_Dose is expressed as a percentage of some maximum time-weighted average for sound pressure level exposure.

Because the sound pressure level dose is cumulative, there is no fixed time-period for ear fatigue or damage. At or below effective quiet, the sound pressure level exposure time would theoretically be infinite, while the time period for achieving the maximum allowable sound pressure level dose becomes smaller and smaller with exposure to increasingly more intense sound. A tolerable level change threshold corresponding to the amount of noise above or below the effective quiet, which has no great effect on the ear as compared to effective quiet, is determined and stored in memory 127 in a step 320. In a step 322, the differential between the weighted sound pressure level and the effective quiet is compared to the level change threshold.

A differential value A, corresponding to the level change, can be calculated as follows:

$$A=\text{SPL\_}W(n)-\text{PSL} \quad (11)$$

If A is greater than the level change threshold, the noise is considered to increase risk for hearing damage and the sound pressure level dose is calculated in a step 324 as follows:

$$\text{SPL Dose}(n)=\text{SPL Dose}(n-1)+(\text{Update\_Epoch}(n)/\text{Time\_100\%}) \quad (12)$$

where SPL Dose(n−1) is the SPL Dose calculated during the last epoch; Update_Epoch is the time (in hours) since the last SPL Dose was calculated. As described above, Update_Epoch can be adaptive, e.g., shortened when the sound pressure level is higher; and Time_100% (n), the time period remaining for safe exposure is determined by the equation:

$$\text{Time\_100\%}(n)=24\ \text{hours}/(2^{((L-\text{PSL})/3)}) \quad (13)$$

where L=sound level (in dB) of the combination of environmental noise and audio playback. It should be noted that sound level (L) can be substituted for SPL_W(n).

It should be noted, as can be seen from the equation, that the time value becomes more important than the sound pressure level as updates are spread apart. However, this is to protect overexposure to harmful sounds because a less accurate sample size must account for the unknown. The wider the periodicity, the less accurate determination of actual exposure. Infrequent updates of the SPL Dose assume a relatively constant sound level, ignoring transients (e.g. spikes) and intervening restorative periods. Accordingly, sound pressure level and epoch periodicity are weighed against each other to protect the ear.

If in step 322 it is determined that the differential is not greater than the level change threshold, including negative values for A (which are restorative values), then in step 326 it is determined whether or not the differential, as determined in step 316, is less than the level change threshold in a step 322. If it is determined that the differential is not less than the level change threshold, then the received noise was the effective quiet level, i.e., the level change threshold equals zero and in a step 330, the current SPL Dose is maintained at the same level. There is no change to the dose level. However, if the differential A is less than the level change threshold then this is a restorative quiet as determined in step 326. Thus, if the differential A (e.g., A=SPL_W(n)−PSL) is less than zero, within measurement error, then this is considered a restorative quiet, then the n-th SPL dose is determined, at step 328, as $$\text{SPL Dose}(n)=\text{SPL Dose}(n-1)*e^{(-\text{Update\_epoch}/\tau)} \quad (14)$$

where: τ (referred to as "tau" in the following diagrams) can vary (e.g., equal to about 7 hours). In some exemplary embodiments, tau is adaptive for different users. In at least one exemplary embodiment, the level change threshold (e.g., measurement error) is set at substantially 0.9-1.0 dB.

Note that other forms of a recovery function can be used and the description herein is not intended to limit the recover function to an exponential relationship. For example, during lower exposure times (e.g., 102 minutes) some SPL values (e.g., 95 dB) can be used, if the subsequent SPL is less than PSL, in a linear manner (for example linearly decreasing until there is a near zero threshold shift at 4000 Hz after one day from the time at which SPL<PSL).

Another non-limiting example of a recovery function can be a combination over certain exposure and decay periods (e.g., 7 day exposure at 90 dB, with an initial threshold shift after the 7 days of about 50 dB at 4000 Hz). For example a slow decaying linear relationship can be applied for the first few hours (e.g., 2 hours) where SPL<PSL, then an exponential decay from after the first few hours to a few days (e.g., 4 days) after which a leveling trend can occur.

Additionally although a fractional increase in SPL Dose is given as a non-limiting example, SPL Dose increase can be linear or exponential depending upon the exposure SPL level and the duration. For example the growth can be linear at a certain SPL values (e.g., 95 dB) during different ranges of exposure time (e.g., for 95 dB, from about 4 minutes to 12 hours), then leveling out (e.g., threshold shift of about 59.5 dB) when the exposure time exceeds a certain length (e.g., for 95 dB about 12 hours).

In at least one exemplary embodiment the SPL values measured by an ECM (e.g., in an ECM mode) can be modified by a modification value (e.g., additive or multiplicative), for example $SPL_{new}=\beta SPL_{old}+\delta$, where the values, $\beta$ and $\delta$, can be time variant, positive or negative. Alternatively the values can be applied to the measured pressure values in a similar manner. One can convert the SPL measured by an ECM to free field values, which then can be compared to free field standards for damage risk criteria. For example Table 1 lists several frequency dependent responses of an earpiece while inserted, the "A" weighting curve offset, and the modification values $\beta$ and $\delta$.

TABLE 1

| Freq. (Hz) | Earpiece Freq. Resp. (dBSPL/V) | "A" weight offset (dB) | β (dB) | δ (dB) |
|---|---|---|---|---|
| 100 | 95 | −19.1 | 1.0 | 0.00 |
| 500 | 103.5 | −3.2 | 1.0 | −0.13 |
| 1000 | 104.0 | 0.0 | 1.0 | −1.83 |
| 2000 | 121.0 | 1.2 | 1.0 | −7.84 |
| 4000 | 106.0 | 1.0 | 1.0 | −15.57 |

Thus, for example an SPL (f) measured at 80 dB, at f=1000 Hz, would be subtracted by −1.83 to obtain a free field value to compare with damage-risk criteria, thus obtaining an $SPL_{new}$ of 78.13 dB. Note what is described is a non-limiting example, various other earpieces can have different values, and the SPL_DOSE equations, described herein, (e.g., SPL_Dose(n), Time_100%) can be based upon $SPL_{new}$. Note that further discussions concerning frequency responses and free field estimate (FFE) conversion can be viewed in U.S. Pat. No. 6,826,515, Bernardi et al. Alternatively ear canal dBA SPL (e.g., as measured by an ECM) may be converted to FFE dBA SPL using Table 1 of ISO 11904-1 (2002), incorporated herein by reference.

In step 332, the recovery time constant tau is determined. It may not be a function of exposure, but rather of recovery. It can be a default number or be determined as will be discussed below. As the SPL Dose is calculated by system 100, it is also monitored. Once the SPL Dose reaches a certain level, as it is a cumulative calculation, ear fatigue calculator 130 determines whether or not the SPL Dose corresponds to a fatigued ear, and if so, it outputs warnings as discussed in connection with FIG. 1.

Figure 5:
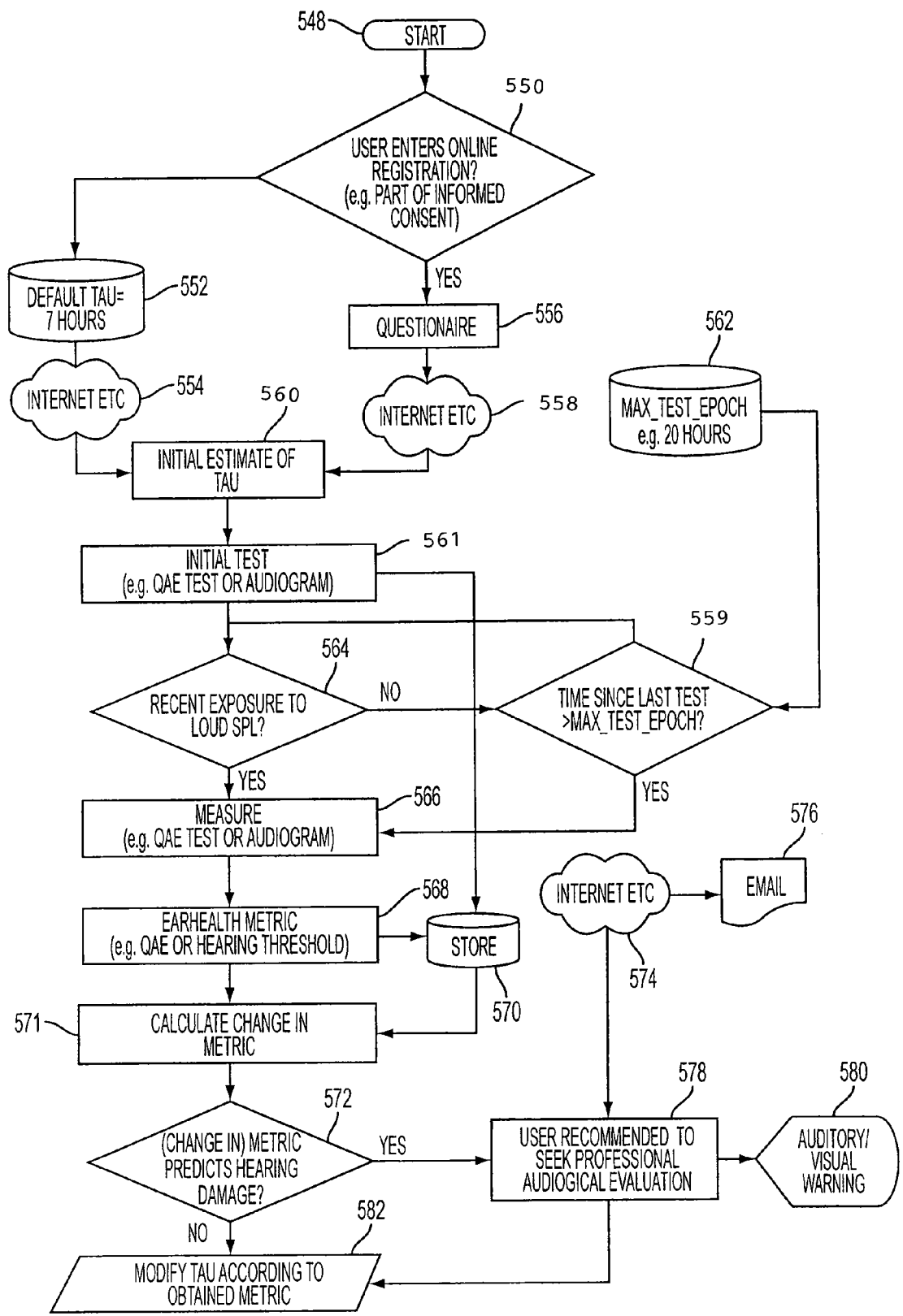
FIG. 5 is a flow chart for determining a personalized recovery time constant in accordance with another exemplary embodiment of the invention.

Reference is now made to FIG. 5 which depicts an optional methodology for not only updating the recovery time constant (tau) for individual users, but to provide additional methods for acting upon detected damaging exposure. The process is started at a step 548. In a step 550, it is determined whether or not the user wishes to make use of a registration process, for example online, for setting a personalized update epoch through communication with a remote registration system. If the user declines the registration, then the default tau is set at 7 hours in a step 552. In a step 554, this default value is transmitted to system 100 via a wired or wireless data communication network.

Alternatively, if the user registers in step 550, a questionnaire is presented in a step 556 in which the user informs system 100 regarding a user sound exposure history, age, work habits and other personal details that could affect the user's personal recovery function time, i.e., the time constant tau. The individual characteristics can be input to a formula or utilized as part of a look up table to determine the tau for the individual user. The estimate of tau determined in step 556 is transmitted to system 100 via a wireless or wired data communication system in a step 558. In step 560, the initial estimate of tau is set from the value determined in step 556 (or step 552).

An initial hearing test is performed in a step 561, which acquires data indicative of the user's hearing sensitivity and/or auditory function. The test may be an otoacoustic emission (OAE) test or audiogram administered utilizing the ear canal receiver or speaker 25. However, the test can also be administered over the Internet, telephone or other communication device capable of outputting sounds sent across a distributed network and enabling responsive communication. The data is stored in a computer memory as an initial test value in a step 570 and is used in further processing to detect a change in the user hearing response.

In a step 564, it is determined whether the user has been recently exposed to intense sound pressure levels. This can be done utilizing the sound pressure level dose as stored or permanently calculated by system 100. If it is decided in step 564 that the user's ear canal sound pressure level is low, then in a step 559 it is determined whether the time since the last test is greater than a maximum test epoch. At the outset, the maximum test epoch is a set number determined in a step 562. In this non-limiting example, the maximum test epoch is set at 20 hours.

If it is determined that the time since the last test is greater than the maximum test epoch or, that there has been recent exposure to intense sound pressure level, then another test is administered in a step 566. The resulting test metrics are stored in steps 568, 570. In a step 571, the newly determined test metrics are compared to the initial test metrics to calculate any change in the metrics. In step 572, it is determined whether the change is predictive of hearing damage. If not, then in a step 582, the tau is modified according the obtained metric.

If it is determined that hearing damage is predicted, then in a step 578 the user is recommended to remove themselves from the noise as discussed above with the operation of listening fatigue calculator 130 and furthermore, the user can be recommended to seek professional audiological evaluation in a step 578. This could be done by an in situ auditory or visual warning in step 580 by system 100. On the other hand, if system 100 is used in connection with a communications device such as a telephone or a personal digital assistant, an e-mail can be created in steps 574, 576; not only warning the user of potential damage, but notifying a health professional so that a follow up examination can be performed.

It should be noted that a change in the hearing metric (e.g., a hearing sensitivity curve) is measured by system 100. In response to the user's hearing metric, the recovery time constant tau is updated. For example, tau is lengthened if the change in the user's hearing metric indicates the user has "sensitive ears", i.e., if, following intense sound exposure, the user's hearing sensitivity takes longer than the exponential function with time-constant of seven hours to return to the individual's normal. This modified tau can be used to calculate the sound pressure level dose, in particular in a restorative phase, to determine a better overall effect of sound pressure level exposure.

By providing a monitoring and protective system which, in at least one mode, continuously monitors sound pressure level at the ear until a potentially harmful exposure has occurred, rather than only monitoring for a predetermined time as with noise dose monitors which monitor for work shifts, a more accurate predictor of harm to the ear is provided. By utilizing a method, which determines exposure in part as a function of effective quiet exposure as well as intense noise exposure, an enhanced model of potential risk is achieved. By providing a series of warning mechanisms and preventive measures as a function of the determined potentially harmful dosage levels ear damage is more likely to be prevented. By providing the system in an earpiece which substantially occludes the ear and making use of audio inputs at the lateral and medial portions of the ear canal (particularly with an occluding device between lateral and medial portions of the ear canal), a more accurate reading of noise level is provided and more control through a real time warning system is achievable.

It should be known that values for level change threshold, effective quiet time, and epoch were used above as examples. However, it should be noted that any values which when input and utilized in accordance with the methodologies above prevent permanent damage to the ear are within the scope of the invention and the invention should not be so limited to the specific examples above.

FURTHER EXEMPLARY EMBODIMENTS

Figure 8:
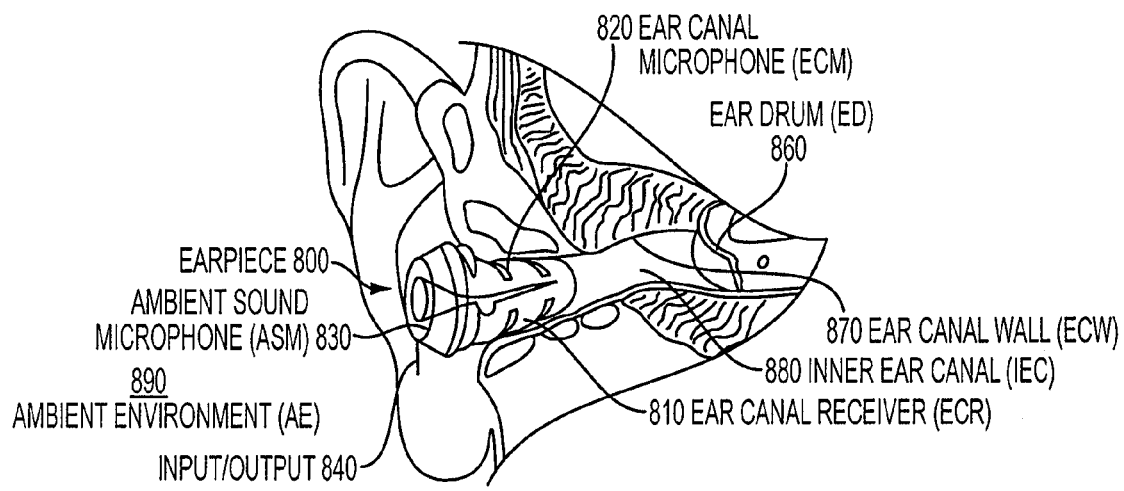
FIG. 8 illustrates the general configuration and terminology in accordance with descriptions of exemplary embodiments.

FIG. 8 illustrates the general configuration and some terminology in accordance with descriptions of exemplary embodiments. An earpiece 800 can be inserted into an ear canal separating the ambient environment (AE) 890 from an inner ear canal (IEC) 880 region, where a portion of the earpiece 800 touches a part of the ear canal wall (ECW) 870. The earpiece 800 can be designed to vary its distance from the eardrum (ED) 860. The earpiece 800 can have various elements, and the non-limiting example illustrated in FIG. 8, can include three sound producing or receiving elements coupled to input/output 840: an ambient sound microphone (ASM) 830 configured to sample the AE 890; an ear canal microphone (ECM) 820 configured to sample the IEC 880; and an ear canal receiver (ECR) 810 configured to acoustically emit into the IEC 880.

Figure 9A:
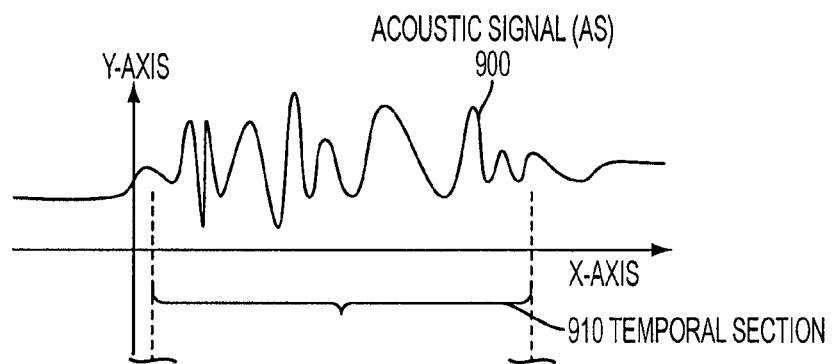
FIGS. 9A-9C illustrates an example of a temporal acoustic signal and its conversion into a spectral acoustic signature.
Figure 9B:
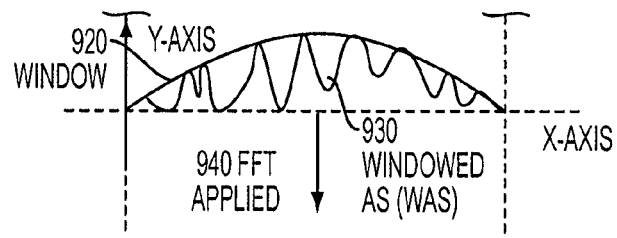
Figure 9C:
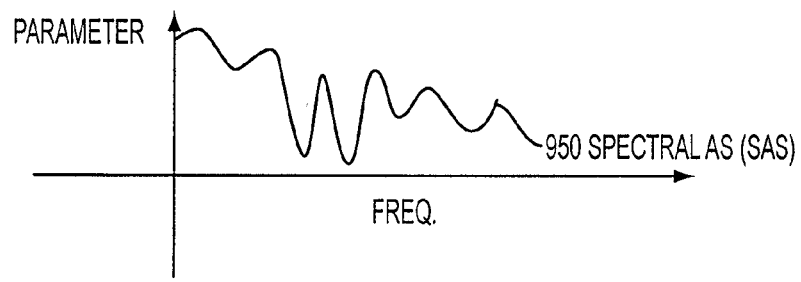

FIGS. 9A-9C illustrates an example of a temporal acoustic signal and its conversion into a spectral acoustic signature. FIG. 9A illustrates a temporal acoustic signal (AS) 900 on a generic X-Y coordinate system (e.g., Y can be amplitude in dB, and X can be time in sec). A section 910 of the AS 900 can be selected for further processing (e.g., for applying filtering treatments such as a FFT). For the non-limiting example of using a Fast Fourier Transform (FFT) on section 910, a window 920 can be applied to the section 910 to zero the ends of the data, creating a windowed acoustic signal (WAS) 930. An FFT can then be applied 940 to the WAS 930 to generate a spectral acoustic signal (SAS) 950, which is illustrated in FIG. 9C, where the Y-axis is a parameter (e.g., normalized power) and the X-axis is frequency (e.g., in Hz).

Figure 10:
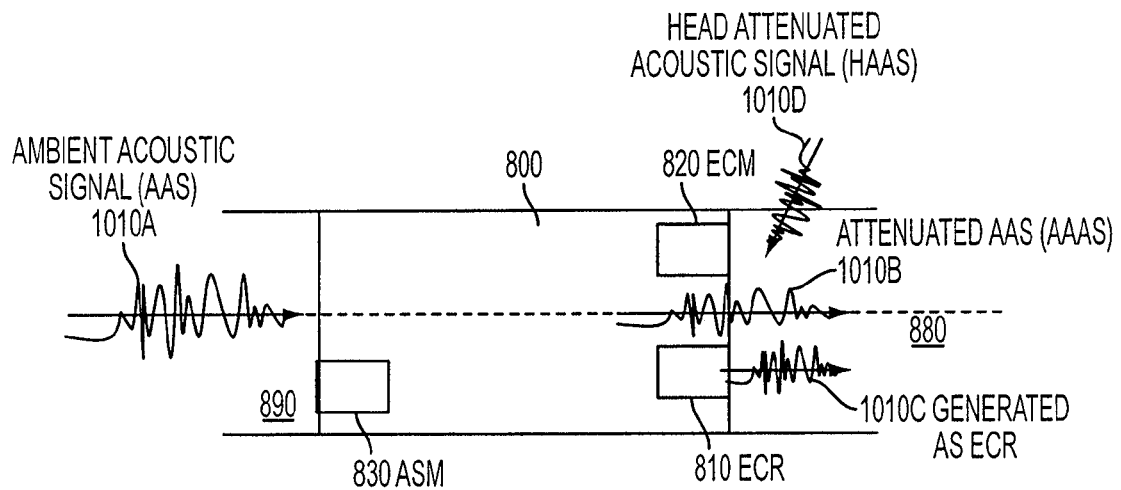
FIG. 10 illustrates a generalized version of an earpiece and some associated parts in an ear canal.

FIG. 10 illustrates a generalized version of an earpiece 800 and some associated parts (e.g., ASM 830, ECM 820, and ECR 810) in an ear canal. When inserted the earpiece 800 generally defines the two regions 890 and 880. Through the earpiece 800 there is some attenuation. For example, an ambient acoustic signal (AAS) 1010A, will travel through the earpiece 800 and/or via bone conduction (not shown) and be attenuated forming an attenuated ambient acoustic signal (AAAS) 1010B. The AAAS 1010B then travels to the ED 860. The other additional acoustic signal 1010C (e.g., the ECR generated AS or ECRAS), which can travel to the eardrum 860, can be generated by the ECR 810. Thus the total AS imparting energy upon the ED 860 can be due to the AAAS 1010B (which can include a bone conduction part not in the IEC 880) and the ECRAS 1010C. Various exemplary embodiments can calculate SPL Dose due to the total imparting AS upon the ED 860, using various combinations of elements (e.g., parts) such as the ECR 810 (e.g., Knowles FG3629), the ECM 820 (e.g., Knowles FK3451), and the ASM 830 (e.g., Knowles FG3629). Note that ECM 820 can also measure head attenuated acoustic signals (HAAS) 1010D, which for example could originate from voice.

During operation, a personal audio device outputs a driving signal to ECR 810 so that ECR 810 outputs an acoustic signal 1010C. Similarly, ASM 830 converts the ambient environment noise into an environmental noise signal, which is input to ECR 810 to generate an ECR ambient sound acoustic signal, which could make up a part of acoustic signal 1010C. ECM 820 receives an ambient acoustic signal AAS 1010B and the ECR-generated signal 1010C and converts it into a total acoustic sound signal to be operated on by earpiece 800 as discussed below.

Figure 11:
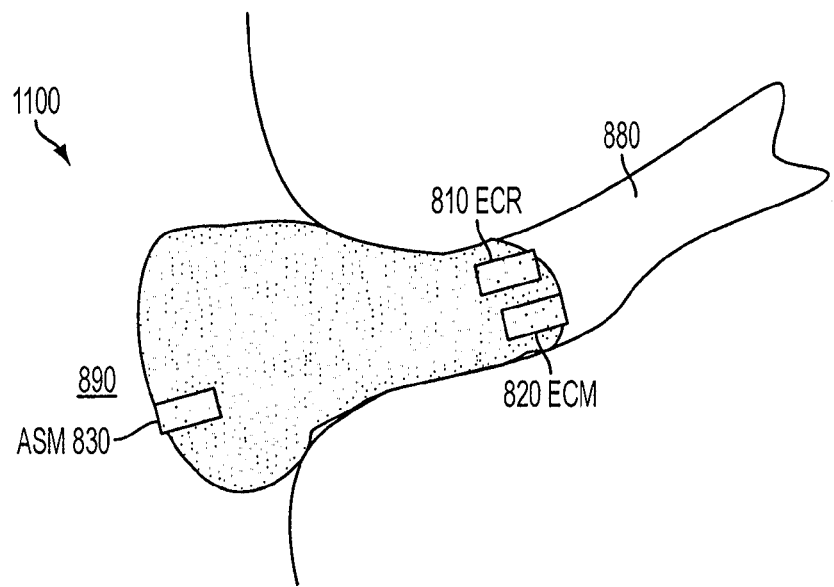
FIG. 11 illustrates an earpiece according to at least one exemplary embodiment.
Figure 12:
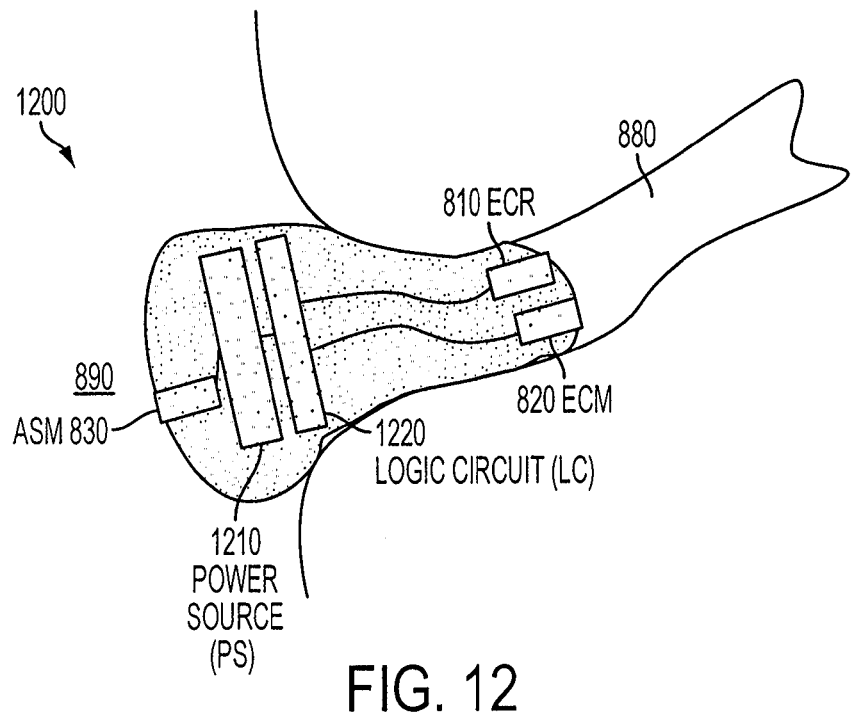
FIG. 12 illustrates a self-contained version of an earpiece according to at least one exemplary embodiment.
Figure 13:
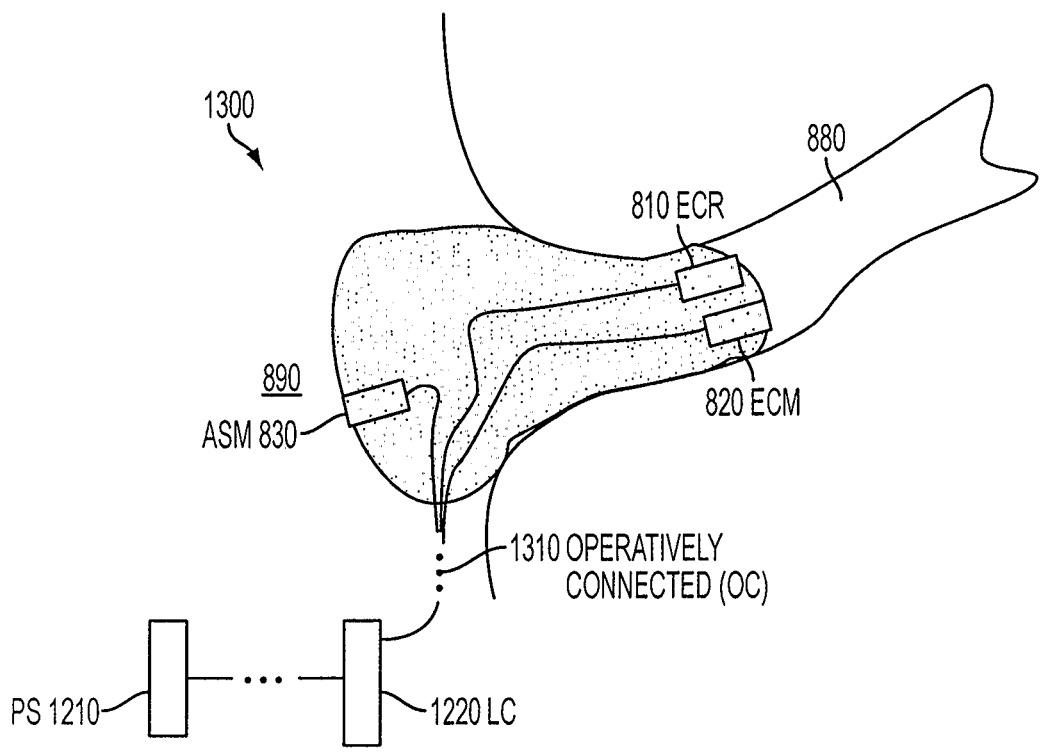
FIG. 13 illustrates an earpiece where parts are not contained in the earpiece directly according to at least one exemplary embodiment.

FIG. 11 illustrates an earpiece 1100 according to at least one exemplary embodiment including an ECR 810 and an ECM 820. ECRAS 1010C generated by the ECR 810 can be predicted and used to predict an equivalent SPL Dose as discussed later. Note that additional elements (e.g., logic circuit(s) (LC), power source(s) (PS), can additionally be included in the earpiece 1100). For example FIG. 12 illustrates a self-contained version of an earpiece 1200 according to at least one exemplary embodiment, including a power source (PS) 1210 (e.g., zinc-air battery (ZeniPower A675P), Li-ion battery), and a logic circuit (LC, e.g., Gennum Chip GA3280) 1220 in addition to ECR 810. Earpiece 1200 can also include a wireless module for wireless communications (not shown) or can be wired. Earpiece 1200 can also connect remotely to various parts (e.g., via a wired or wireless connection). For example FIG. 13 illustrates an earpiece 1300 where parts are not contained in the earpiece directly according to at least one exemplary embodiment. As illustrated the LC 1220 and PS 1210 are operatively connected (OC) 1310 (e.g., via a wire or wirelessly) to the earpiece 1300. For example earpiece 1300 can be an earbud that includes ECR 810, whose signals travel back and forth via a wire that is operatively connected via a wire to LC 1220, which in turn can be operatively connected to PS 1210. Note that ECR 810 can also be a dual purpose ECR/ECM, where when the receiver function (ECR mode) is not used the microphone function (ECM mode) can be used. For example U.S. Pat. No.

3,987,245 discusses a dual-purpose transducer that can be used as a microphone and/or a receiver.

Figure 14A:
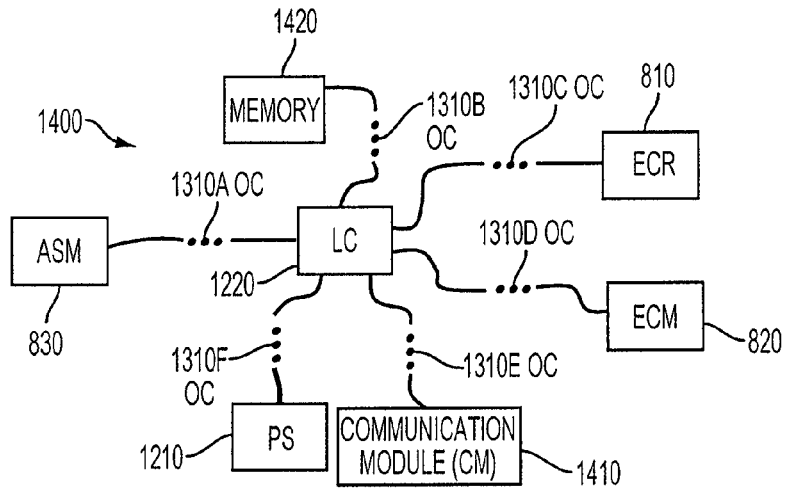
FIG. 14A illustrates a general configuration of some elements of an earpiece according to at least one exemplary embodiment.

FIG. 14A illustrates a general configuration of some elements of an earpiece according to at least one exemplary embodiment. Again, like numerals are utilized to indicate like structure in which an earpiece 1400 includes a logic circuit 1220. Logic circuit 1220 has an operative connection 1310A to ASM 830; operative connection 1310B to a memory 1420; operative connection 1310C to ECR 810; operative connection 1310D to ECM 820; operative connection (e.g., operatively connected) 1310E to a communication module 1410; and an operative connection 1310F to a power source 1210. Again, it should be noted that the operative connection could be either wireless or hard wired and that as discussed above, elements other than ECR 810 could be remote from earpiece 1400. It should be understood that ASM 830 cannot be too remote from the ear of the user in order to properly measure the ambient sound and ambient environment 890.

Figure 14B:
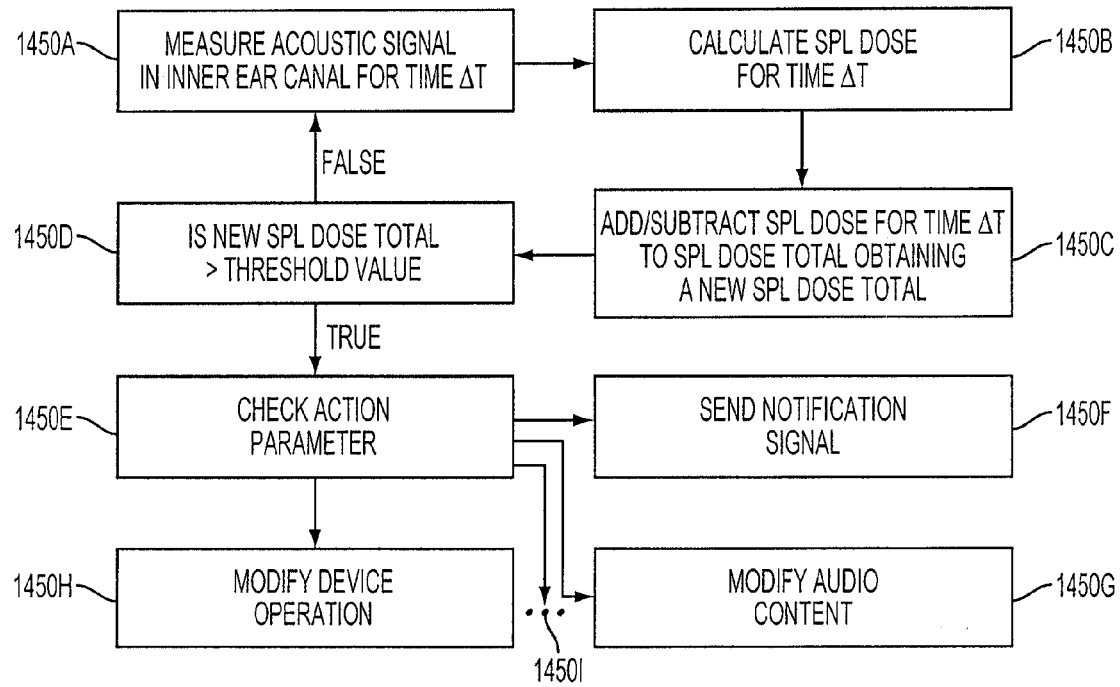
FIG. 14B illustrates a flow diagram of a method for SPL_Dose calculation according to at least one exemplary embodiment.

ECM 820 measures the noise level as it exists in inner ear canal 880. This includes ambient sound as attenuated by earpiece 800 and/or any sound produced by ECR 810 from an associated Personal Acoustic Device or from ASM 830. FIG. 14B illustrates a flow diagram of a method for SPL_Dose calculation and response according to at least the exemplary embodiments of earpieces 1100-1300; i.e., using only ECM 820. Logic circuit 1220 and the other elements are powered by power source 1210. Logic circuit 1220 processes signals as received from ECM 820. Logic circuit 1220 may make use of controls, weighting curves, and stored values as discussed above, in order to process the acoustic signals detected by ECM 820.

Total SPL_Dose is a function of both ambient noise and any driving signals delivered to ECR 810 or ECM 820 from a connected personal audio device such as a cell phone or music player. Therefore, in accordance with the invention, in a first step 1450A, the detected acoustic signal detected in inner ear canal 880 is measured for a time period ΔT.

In a step 1450B, an SPL_Dose equivalent is calculated for the time period Δt in accordance with any of the exemplary methods discussed herein. In a step 1450C, the SPL_Dose for the time period is added to, or subtracted from, the current Total SPL_Dose to obtain a new Total SPL_Dose. In this way the total is continuously updated and monitored. It is understood that if the SPL_Dose for the time period is a restorative dose, then the effect during the time period Δt is negative relative to damage and therefore is subtracted from the Total SPL_Dose at time t to obtain the new Total SPL_Dose. Conversely, if the calculated exposure during the time period is greater than a permissible sound level (PSL), the SPL_Dose for the current time period Δt is considered potentially damaging and will be added to Total SPL_Dose.

In a step 1450D, it is determined whether or not the Total SPL_Dose is greater than a threshold value. If the Total SPL_Dose has not increased to more than a threshold value, then the process is repeated in step 1450A. If the Total SPL_Dose is greater than the threshold value then logic circuit 1220 checks for action parameters to be taken in a step 1450E. An action parameter corresponds to the corrective action to be taken.

In a step 1450F, the action parameter could correspond to sending a notification signal such as an audio signal, output by ECR 810, ECM 820, or a visual notification on the associated personal audio device. Alternatively, the action parameter could correspond to modifying the audio content through attenuation in a step 1450G as discussed above. Furthermore, the action parameter could correspond to modifying the operation of the personal audio device itself in a step 1450H in which the device either shuts off or attenuates its output signal at its origination rather than attenuating the output signal at ECR 810 or ECM 820 as in step 1450G. Other actions may be taken like those suggested above or others in a step 1450I.

It is well within the scope of the invention to modify the earpiece device in which the ECR 810 or ECM 820 may be utilized to function in both capacities. In other words, the ECM 820 may be used to calibrate the ECR 810, to receive driving signals to function as an ECR in an embodiment in which both the ECR 810 and ECM 820 are simple transducers.

Additionally, ECM 820 may be utilized to detect the user's own voice as it is perceived within inner ear canal 880. Logic circuit 1220 distinguishes between the user's own voice and the voices of others by determining a difference in the relative intensity of the voices measured by ECM 820. Intensity is a function of the measured SPL_Dose. Therefore, by calculating relative SPL_Dose at ECM 820, logic circuit can differentiate between and account for the voice of the user.

In one non-limiting example, ECM 820 measures acoustic signals below a certain threshold such as 40-50 dB. This is most likely, in one embodiment, lower than the received speaking voice SPL of the user of earpiece 800 at ECM 820. Therefore, logic circuit 1220 determines that voice frequencies at SPL levels below this threshold are not the speaking voice of the user. Of course, the predetermined threshold level can be tuned from user to user depending upon their range of speaking voice from whisper to shout.

In another embodiment, ASM 830 can also measure the voice of the user as a part of ambient environment 890 and compare that value to the SPL of the voice of the user as measured in the inner ear at ECM 820. The SPL_Dose measured attributable to the user's voice within the inner ear should be greater than the value of the voice as part of the ambient environment 890. Therefore, logic circuit 1220 determines whether the ECM SPL_Dose is greater than the ASM SPL_Dose to determine whether or not words received belong to the user or a third party.

An Example of Calculating SPL

SPL exposure within the ear canal in accordance with the invention is a function of noise from both the ambient environment and generated within the ear canal by ECR 810 as a function of input signals thereto. An accurate way to measure SPL exposure is to actually measure the noise level in inner ear canal 880. Accordingly estimated SPL_Dose may be calculated in one embodiment as follows:

$$\text{SPL\_Dose}_{ECM+ASM} = \text{SPL\_Dose}_{ECM+ASM-1} + \text{Time of Sound Exposure/Time 100\%} \quad (15)$$

where Time $100\% = 24 \text{ hrs}/2^{((L_{ECM+ASM}-80)/3)}$ where $L_{ECM+ASM}$ is the measured Ear Canal d/BA SPL by the ECM 820 and the ambient SPL by the ASM 830. It is anticipated that the purpose of the ASM 830 will be to allow pick-up of environmental sound, but not necessarily contribute to the determination of SPL_Dose in this embodiment. Hence, $L_{ECM+ASM}$ may be analogous to $L_{ECM}$ alone. So $\text{ASM}_{-1}$ and ASM go to zero over time and only the ECM component need be accounted for. Thus, the SPL_Dose can contain only measured components from the ECM 820. If for some reason the ECM 820 can not be used, a backup value of SPL measured by the ASM 830 corrected for NRR of the earpiece added to estimated SPL emitted by the ECR 810 can be used as a less accurate value of using the SPL value measured by the ECM 820. The Time of Sound Exposure is the time during which $L_{ECM+ASM}$ occurs.

The value of 80 in determining the time is a threshold value of interest for decibels of the sound level in this one exemplary embodiment. As discussed above, 80 does have some significance to audiologists, but the number may also be the effective quiet, or any other level predetermined by a person skilled in the art designing the system as a function of noise exposure a user will be allowed to experience.

In at least one exemplary embodiment one can determine a Free Field Equivalent (FFE) dBA SPL for purposes of determining pressure level dose, the ear canal dBA SPL may be converted to FFE dBA SPL using Table 1 of ISO 11904-1 (2002).

Figure 15A:
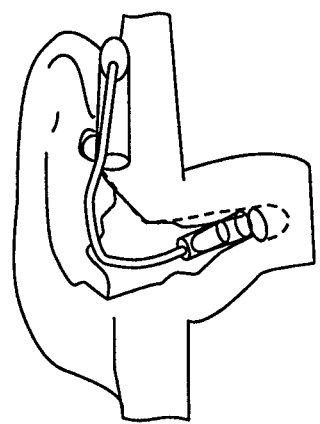
FIGS. 15A to 15N illustrate various non-limiting examples of earpieces that can use methods according to at least one exemplary embodiment.
Figure 15B:
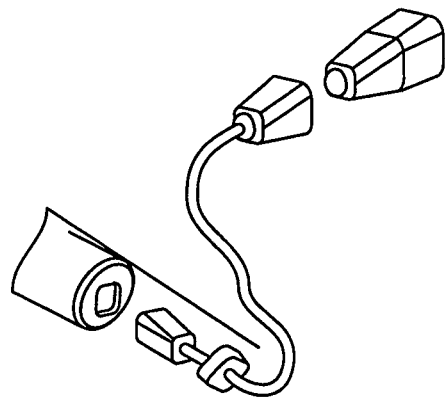
Figure 15C:
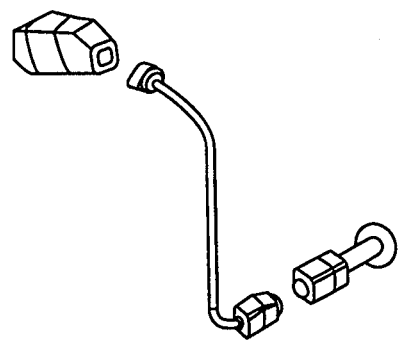
Figure 15D:
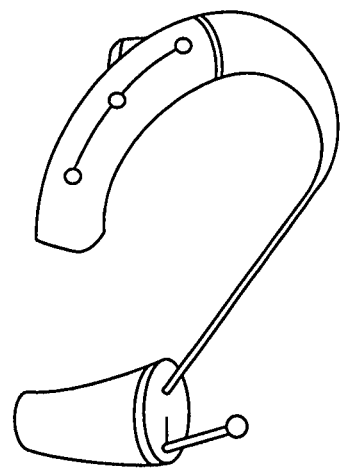
Figure 15E:
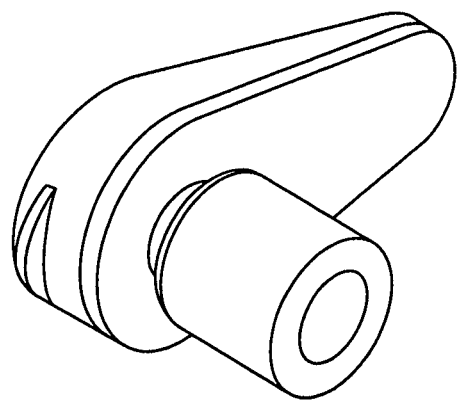
Figure 15F:
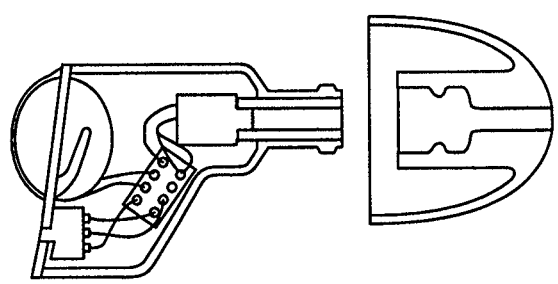
Figure 15G:
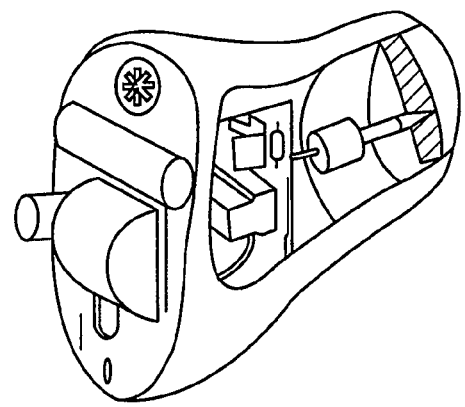
Figure 15H:
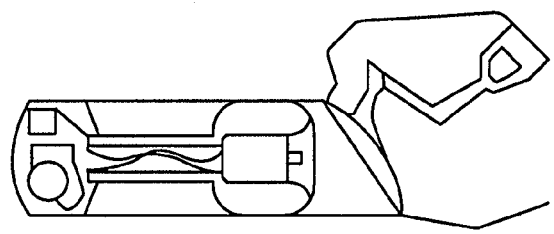
Figure 15I:
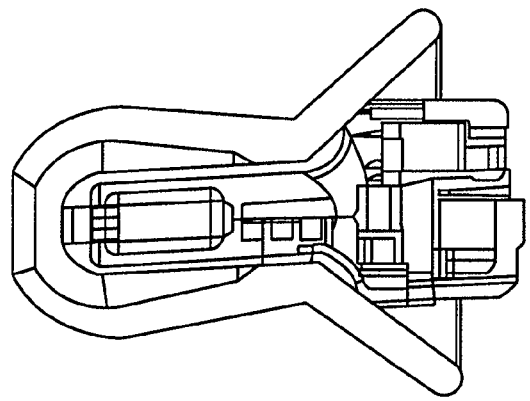
Figure 15J:
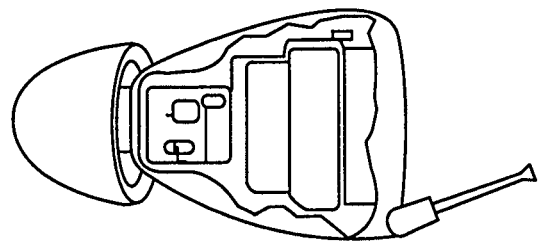
Figure 15K:
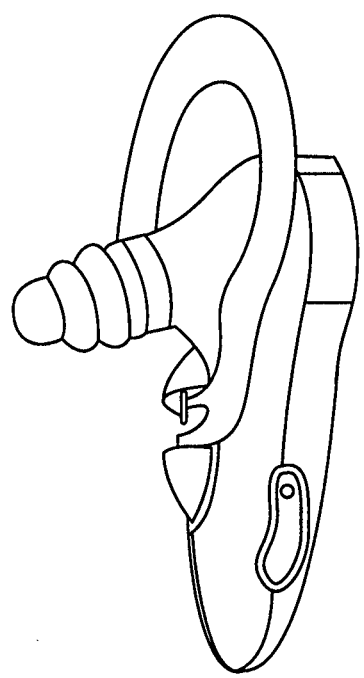
Figure 15L:
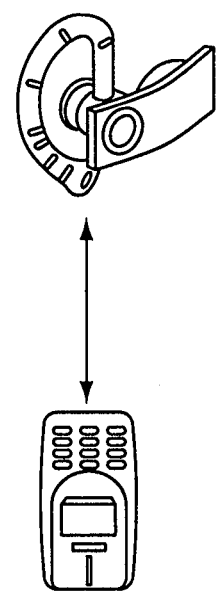
Figure 15M:
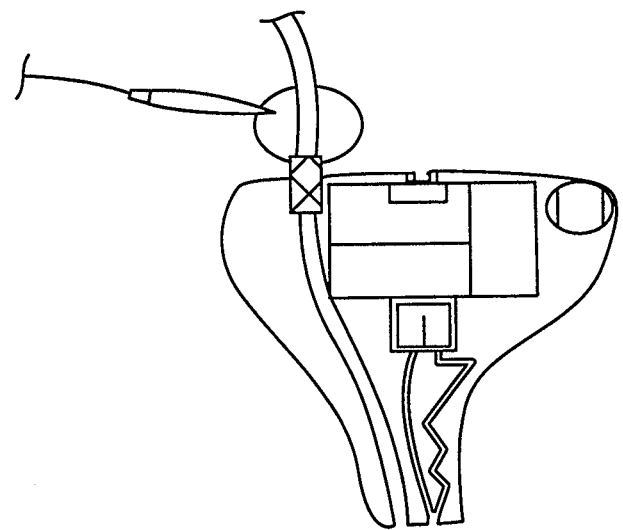
Figure 15N:

Exemplary embodiments of the present invention can be used in many platforms that direct and/or attenuate acoustic energy in the ear canal. FIGS. 15A to 15N illustrate various non-limiting examples of earpieces that can use methods according to at least one exemplary embodiment, when the various earpieces have an ECR 810 and an ASM 830.

Figure 16:
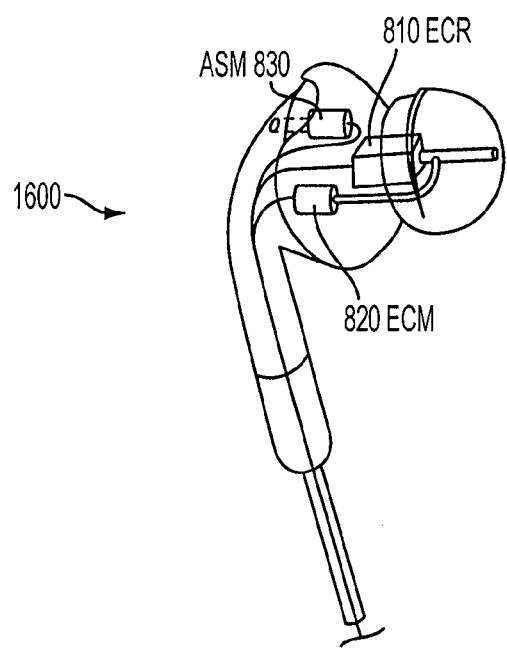
FIG. 16 illustrates a line diagram of an earpiece (e.g., earbud) that can use methods according to at least one exemplary embodiment.
Figure 17:
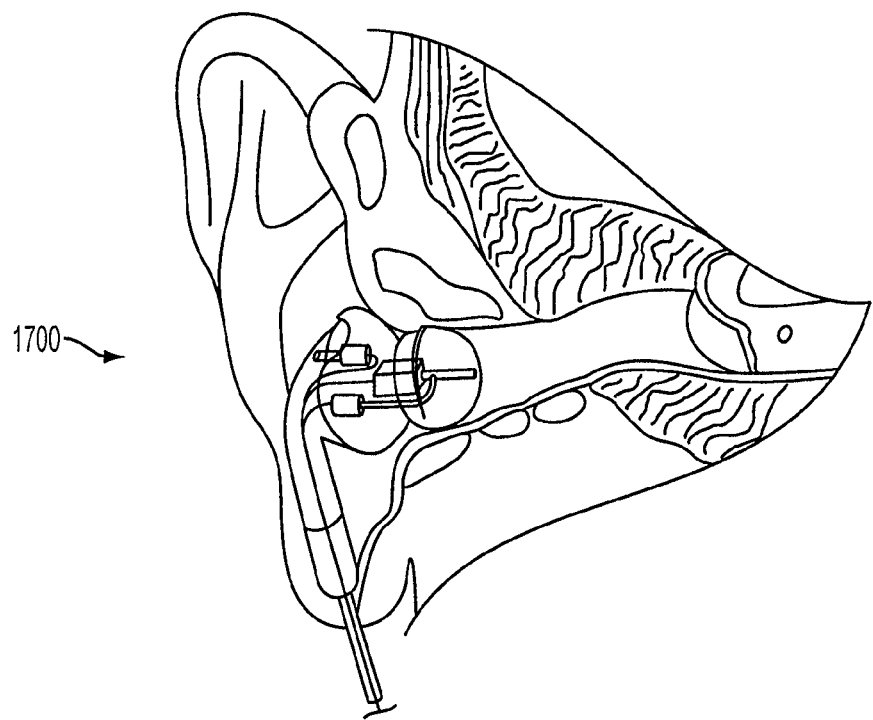
FIG. 17 illustrates the earpiece of FIG. 16 fitted in an ear.

FIG. 16 illustrates a line diagram of an earpiece 1600 (e.g., earbud) that can use methods according to at least one exemplary embodiment and FIG. 17 illustrates the earpiece 1700 of FIG. 16 fitted in an ear canal. Earbuds can be used with many devices such as audio playback devices, PDAs, phones, and other acoustic management devices. The software to implement exemplary embodiments can reside in the earpiece (e.g., hearing aid) or can reside in the acoustic management systems (e.g., iPod™, Blackberry™, and other acoustic management devices as known by one of ordinary skill in the relevant arts).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions of the relevant exemplary embodiments. For example, although specific numbers may be quoted in the claims, it is intended that a number close to the one stated is also within the intended scope, i.e., any stated number (e.g., 80 dB) should be interpreted to be "about" the value of the stated number (e.g., about 80 dB). Thus, the description of the invention is merely exemplary in nature and, thus, variations that do not depart from the gist of the invention are intended to be within the scope of the exemplary embodiments of the present invention. Such variations are not to be regarded as a departure from the spirit and scope of the present invention.

What is claimed is:

1. A method of determining an onset of a voice of a user comprising:
   measuring ambient sound pressure levels (SPLs) over a time period having a plurality of samples with an ambient sound microphone (ASM) positioned at an entrance to an ear canal of the user;
   measuring ear canal SPLs over the time period with an ear canal microphone (ECM) positioned within the ear canal;
   determining a first SPL dose from the ambient SPLs and a second SPL dose from the ear canal SPLs over the time period, each of the first SPL dose and the second SPL dose being determined based on a corresponding previous SPL dose in a previous time period and a corresponding safe exposure time period, the safe exposure time period being determined using the respective ambient SPLs or the ear canal SPLs, the safe exposure time period representing a remaining time of sound exposure until a predetermined dosage is reached; and
   comparing the first SPL dose and the second SPL dose for at least one voice component to determine whether the at least one voice component is produced from the voice of the user.

2. The method of claim 1, wherein it is determined that the at least one voice component is due to the user when the second SPL dose is greater than the first SPL dose.

3. The method of claim 1, wherein it is determined that the at least one voice component is due to the user when the ear canal SPLs for the at least one voice component are greater than 80 dB.

\* \* \* \* \*